(12) United States Patent
Kanai et al.

(10) Patent No.: US 10,190,172 B2
(45) Date of Patent: Jan. 29, 2019

(54) METHOD FOR DETERMINING PROGNOSIS OF RENAL CELL CARCINOMA

(71) Applicants: NATIONAL CANCER CENTER, Chuo-ku (JP); SEKISUI MEDICAL CO., LTD., Chuo-ku (JP)

(72) Inventors: Yae Kanai, Koto-ku (JP); Eri Arai, Bunkyo-ku (JP); Yuriko Nemoto, Chiba (JP); Takuya Yotani, Ibaraki (JP)

(73) Assignees: NATIONAL CANCER CENTER, Chuo-ku (JP); SEKISUI MEDICAL CO., LTD., Chuo-ku (JP)

( * ) Notice: Subject to any disclaimer, the term of this patent is extended or adjusted under 35 U.S.C. 154(b) by 20 days.

(21) Appl. No.: 15/121,656

(22) PCT Filed: Mar. 2, 2015

(86) PCT No.: PCT/JP2015/056108
§ 371 (c)(1),
(2) Date: Aug. 25, 2016

(87) PCT Pub. No.: WO2015/129916
PCT Pub. Date: Sep. 3, 2015

(65) Prior Publication Data
US 2017/0058355 A1 Mar. 2, 2017

(30) Foreign Application Priority Data

Feb. 28, 2014 (JP) .................................. 2014-039417
Mar. 7, 2014 (JP) .................................. 2014-044943

(51) Int. Cl.
| | | |
|---|---|---|
| C12Q 1/6827 | (2018.01) | |
| C12Q 1/6886 | (2018.01) | |
| G01N 30/96 | (2006.01) | |
| G01N 30/88 | (2006.01) | |
| B01D 15/36 | (2006.01) | |

(52) U.S. Cl.
CPC ......... *C12Q 1/6886* (2013.01); *B01D 15/362* (2013.01); *C12Q 1/6827* (2013.01); *G01N 30/88* (2013.01); *G01N 30/96* (2013.01); *C12Q 2600/118* (2013.01); *C12Q 2600/154* (2013.01); *G01N 2030/8813* (2013.01)

(58) Field of Classification Search
None
See application file for complete search history.

(56) References Cited

U.S. PATENT DOCUMENTS

| | | |
|---|---|---|
| 5,786,146 A | 7/1998 | Herman et al. |
| 2002/0198372 A1 | 12/2002 | Bridenbaugh et al. |
| 2004/0265814 A1 | 12/2004 | Distler et al. |
| 2014/0030713 A1 | 1/2014 | Yotani et al. |
| 2014/0147842 A1 | 5/2014 | Yotani et al. |
| 2014/0349284 A1 | 11/2014 | Yotani et al. |
| 2015/0118681 A1 | 4/2015 | Kanai et al. |
| 2016/0138097 A1 | 5/2016 | Yotani et al. |

FOREIGN PATENT DOCUMENTS

| | | |
|---|---|---|
| JP | 10-502052 A | 2/1998 |
| JP | 2002-521029 A | 7/2002 |
| JP | 2010-63413 A | 3/2010 |
| WO | 95/27718 A2 | 10/1995 |
| WO | 2012/096329 A1 | 7/2012 |
| WO | 2012/108516 A1 | 8/2012 |
| WO | 2012/133834 A1 | 10/2012 |
| WO | 2013/168644 A1 | 11/2013 |
| WO | 2014/136930 A1 | 9/2014 |

OTHER PUBLICATIONS

Arai (Carcinogenesis, 2012, vol. 33, pp. 1487-1493).*
Jean-Pierre ISSA, "CpG island methylator phenotype in cancer, Nature Reviews Cancer", vol. 4, pp. 988-993, (Dec. 2004).
Minoru Toyota, et al., "CpG island methylator phenotype in colorectal cancer", Proc. Natl. Acad. Sci. USA., vol. 96, pp. 8681-8686, (Jul. 1999).
Lanlan Shen, et al., "Integrated genetic and epigenetic analysis identifies three different subclasses of colon cancer", PNAS, vol. 104, No. 47, Total 17 Pages, (Nov. 20, 2007) (with Supplemental Data).
Minoru Toyota, et al., "Aberrant Methylation in Gastric Cancer Associated with the CpG Island Methylator Phenotype", Cancer Research, vol. 59, Total 6 Pages, (Nov. 1, 1999).
James G. Herman, et al., "Methylation-specific PCR: A novel PCR assay for methylation status of CpG islands", Proc. Natl. Acad. Sci. USA., vol. 93, pp. 9821-9826, (Sep. 1996).
Ramin Sadri, et al., "Rapid analysis of DNA methylation using new restriction enzyme sites created by bisulfate modification", Nucleic Acids Research, vol. 24, No. 24, pp. 5058-5059, (1996).
Zhenggang Xiong, et al., "COBRA: a sensitive and quantitative DNA methylation assay", Nucleic Acids Research, vol. 25, No. 12, pp. 2532-2534, (1997).

(Continued)

*Primary Examiner* — Sarae L Bausch
(74) *Attorney, Agent, or Firm* — Oblon, McClelland, Maier & Neustadt, L.L.P.

(57) ABSTRACT

It is intended to provide a rapid, convenient, and highly accurate method for determining the prognosis of cancer. The present invention provides a method for determining the prognosis of a renal cell carcinoma patient, comprising: (1) treating genomic DNA prepared from a renal tissue of a subject with bisulfite; (2) amplifying the bisulfite-treated DNA by PCR; (3) subjecting the obtained PCR amplification product to ion exchange chromatography; (4) obtaining the retention time of a detection signal obtained by the chromatography; and (5) determining the renal cell carcinoma of the subject as having poor prognosis when the result of the step (4) is shorter than a retention time serving as a reference.

9 Claims, 6 Drawing Sheets
Specification includes a Sequence Listing.

(56) References Cited

OTHER PUBLICATIONS

Eri Arai, et al., "Genetic Clustering of Clear Cell Renal Cell Carcinoma Based on Array-Comparative Genomic Hybridization: Its Association with DNA Methylation Alteration and Patient Outcome", Clin Cancer Res, vol. 14, No. 17, pp. 5531-5539, (Sep. 1, 2008).

Eh Arai, et al., "Regional DNA hypermethylation and DNA methyltransferase (DNMT) 1 protein overexpression in both renal tumors and corresponding nontumorous renal tissues", Int. J. Cancer, vol. 119, pp. 288-296, (2006).

Eri Arai, et al., "Genome-wide DNA methylation profiles in both precancerous conditions and clear cell renal cell carcinomas are correlated with malignant potential and patient outcome", Carcinogenesis, vol. 30, No. 2, 12 Pages, (2009) (with Supplemental Data).

Eh Arai, et al., "Genome-Wade DNA Methylation Profiles in Renal Tumors of Various Histological Subtypes and Non-Tumorous Renal Tissues", Pathobiology, vol. 78, 10 Pages, (2011) (with Supplemental Data).

Kazunari Yasuda, "HPLC Column o Mochiita DNA Methyl-ka Kaisekiho no Kaihatsu, (Development of DNA Methylation Analysis Method Using HPLC Column)", Total 5 Pages, (2013), (with Partial English Translation).

Graham J. R. Brock, et al., "A novel technique for the identification of CpG is ands exhibiting altered methylation patterns (ICEAMP)", Nucleic Acids Research, vol. 29, No. 24, Total 7 Pages, (2001).

International Search Report dated May 26, 2015 in PCT/JP15/056108 Filed Mar. 2, 2015.

Extended European Search Report dated Sep. 18, 2017 in Patent Application No. 15755821.4.

Faranaz Atschekzei, et al., "SFRP1 CpG island methylation locus is associated with renal cell cancer susceptibility and disease recurrence", Epigenetics, vol. 7, No. 5, XP055403445, 2012, pp. 447-457.

Alessandra Baumer, et al., "A novel MSP/DHPLC method for the investigation of the methylation status of imprinted genes enables the molecular detection of low cell mosaicisms", Human Mutation. vol. 17, No. 5, XP055403266, 2001, pp. 423-430.

Maryam M. Matin, et al.. "An analytical method for the detection of methylation differences at specific chromosomal loci using primer extension and ion pair reverse phase HPLC", Human Mutation, Vo. 20, No. 4, XP009043993, 2002, pp. 305-311.

Wilfried Rozhon, et al., "Rapid quantification of global DNA methylation by isocratic cation exchange high-performance liquid chromatography", Analytical Biochemistry, vol. 375, No. 2, XP029160009, 2008, pp. 354-360.

* cited by examiner

A

B

METHOD FOR DETERMINING PROGNOSIS OF RENAL CELL CARCINOMA

FIELD OF THE INVENTION

The present invention relates to a method for determining the prognosis of renal cell carcinoma by use of the detection of methylated DNA.

BACKGROUND OF THE INVENTION

In recent years, abnormal methylation of DNA has been found to be deeply involved in malignant transformation and has received attention. Abnormal DNA methylation of CpG islands in some gene promoter regions is known as a characteristic epigenetic abnormality in cancer cells. The CpG island is a region in which a two-nucleotide sequence of cytosine (C)-guanine (G) via a phosphodiester bond (p) appears with high frequency. This region often resides in a promoter region upstream of a gene. The abnormal DNA methylation of the CpG island is involved in carcinogenesis through the inactivation of tumor suppressor genes, etc. DNA hypermethylation of the CpG island correlating with clinicopathological factors has been reported in colorectal cancer, stomach cancer, etc. (Non Patent Literatures 1 to 4). Such a type of cancer is called CpG island methylation phenotype (CIMP)-positive cancer.

Already established methods for analyzing methylated DNA include a method based on bisulfite reaction. This method is a method most generally used in the analysis of methylated DNA. The treatment of single-stranded DNA with bisulfite converts cytosine to uracil through sulfonation, hydrolic deamination, and desulfonation. On the other hand, methylated cytosine is left unaltered throughout the reaction time of actually performed bisulfite treatment because the reaction rate of sulfonation as the first step is very slow. Thus, PCR (polymerase chain reaction) using the bisulfite-treated DNA amplifies unmethylated cytosine with the uracil replaced with thymine, while leaving the methylated cytosine unaltered. The methylation status is analyzed through the use of the difference between the bases cytosine and thymine appearing in the sequence of this PCR amplification product. Methods generally used according to this basic principle are methylation-specific PCR (MSP) described in Patent Literature 1 and Non Patent Literature 5, and combined bisulfite restriction analysis (COBRA) described in Non Patent Literatures 6 and 7.

The MSP method is a method which involves sequentially performing PCR amplification using a methylated sequence-specific primer and an unmethylated sequence-specific primer and agarose gel electrophoresis after bisulfite treatment of DNA, and determining the DNA methylation status of the target region from the presence or absence of an amplification product derived from both of the primers. The COBRA method is a method which involves sequentially performing PCR amplification using common primers for methylated DNA and unmethylated DNA, treatment using a restriction enzyme recognizing a site differing in sequence between methylated DNA and unmethylated DNA, and agarose gel electrophoresis after bisulfite treatment of DNA, and determining the DNA methylation status of the target region from the presence or absence of the restriction enzyme-treated fragment. Both of these methods are methylated DNA analysis methods currently used widely because these methods are capable of quantitatively analyzing methylated DNA without special equipment. A problem of the methods, however, is time and labor required for electrophoresis used in the analysis.

Meanwhile, ion exchange chromatography is generally used as a method capable of convenient and accurate detection in a short time in the separation and analysis of biomacromolecules such as nucleic acids, proteins, and polysaccharides, for example, in biochemical and medical fields. In the case of separating a PCR amplification product of a nucleic acid by use of ion exchange chromatography, anion exchange chromatography, which separates the PCR amplification product through the use of the negative charge of phosphate contained in the nucleic acid molecule, is generally used. Columns for anion exchange chromatography packed with column packing materials having cationic functional groups as ion exchange groups have already been commercially available and used in various research fields.

It has been further reported that the single-nucleotide difference between 20-mer unmethylated synthetic oligonucleotides can be separated and analyzed by ion exchange chromatography using a column packed with a column packing material having both a strong cationic group and a weak cationic group as cationic functional groups (Patent Literature 2).

Renal cell carcinoma (RCC) often develops even in middle-aged people belonging to the working population. A great majority of RCC case groups are completely cured by nephrectomy, whereas case groups which progress rapidly into distal metastasis are obviously present. These curable and metastatic RCC case groups largely differ in their clinical courses. Furthermore, some of cases with metastasis are known to respond to immunotherapy, molecular targeting therapeutic drugs, or the like. There is the possibility that the prognosis of cases likely to have recurrence can be improved by close follow-up, early diagnosis of recurrence, and additional aftercare. However, some cases experience rapid distal metastasis of clear cell RCC even having a low histopathological grade and a most common histological type. Thus, it is difficult to predict the prognosis of RCC using existing clinicopathological factors or the like.

Analyses by MSP, COBRA, and bacterial artificial chromosome (BAC) array-based methylated CpG island amplification (BAMCA) have showed that noncancerous renal cortical tissues obtained from RCC patients are already at a precancerous stage associated with change in DNA methylation status (Patent Literature 3 and Non Patent Literatures 8 to 11). In addition, genome-wide analysis by BAMCA has also revealed that change in DNA methylation in noncancerous renal cortical tissues at a precancerous stage is inherited to the corresponding RCC in the same patients. A method for predicting the prognosis of an RCC case has been successfully developed (Patent Literature 3 and Non Patent Literature 10).

Recently, it has been found that highly malignant RCC exhibits a CIMP-positive phenotype, and methylation at the CpG sites of 17 genes (FAM150A, GRM6, ZNF540, ZFP42, ZNF154, RIMS4, PCDHAC1, KHDRBS2, ASCL2, KCNQ1, PRAC, WNT3A, TRH, FAM78A, ZNF671, SLC13A5, and NKX6-2) is a feature of CIMP of RCC (Patent Literature 4). Patent Literature 4 has proposed a method for detecting a risk of poor prognosis of RCC by detecting a methylation level at the CpG sites of those 17 genes by bead array method, mass spectrometry (MassARRAY method), pyrosequencing, methylation-sensitive high-resolution melting curve analysis, quantitative PCR, direct sequencing of bisulfite treatment products, COBRA, or the like. The value of a DNA methylation rate obtained by a method conventionally used, such as MassARRAY method or pyrosequencing, is obtained as an average DNA methylation rate of the whole sample subjected to the assay. Therefore, in the case of a sample rich in cells having a low DNA methylation rate, the obtained value of a DNA methylation rate is low even if cells having highly methylated DNA coexist therewith. This causes problems that the presence or absence of cells having highly methylated DNA cannot be determined, and a risk of estimating DNA methylation rates to be lower than actual values cannot be avoided.

CITATION LIST

Patent Literature

[Patent Literature 1] U.S. Patent No. 5786146
[Patent Literature 2] WO 2012/108516
[Patent Literature 3] JP-A-2010-63413
[Patent Literature 4] WO 2013/168644
[Non Patent Literature]
[Non Patent Literature 1] Nat. Rev. Cancer, 4, 988-993 (2004)
[Non Patent Literature 2] Proc. Natl. Acad. Sci. USA, 96, 8681-8686 (1999)
[Non Patent Literature 3] Proc. Natl. Acad. Sci. USA, 104, 18654-18659 (2007)
[Non Patent Literature 4] Cancer Res., 59, 5438-5442 (1999)
[Non Patent Literature 5] Proc. Natl. Acad. Sci. USA, 93, 9821-9826 (1996)
[Non Patent Literature 6] Nucleic Acids Res., 24, 5058-5059 (1996)
[Non Patent Literature 7] Nucleic Acids Res., 25, 2532-2534 (1997)
[Non Patent Literature 8] Clin. Cancer Res., 14, 5531-5539 (2008)
[Non Patent Literature 9] Int. J. Cancer, 119, 288-296 (2006)
[Non Patent Literature 10] Carcinogenesis, 30, 214-221 (2009)
[Non Patent Literature 11] Pathobiology, 78, 1-9 (2011)

SUMMARY OF THE INVENTION

Problem to be Solved by the Invention

For preventing the recurrence of cancer, it is desirable to start treatment by obtaining information on the methylation status of genomic DNA and thereby determining a risk of recurrence with high specificity. If the metastasis and/or recurrence of cancer can be predicted and detected early, response thereof to immunotherapy, molecular targeting therapeutic drugs, or the like can be expected. Therefore, there has been a demand for a method capable of more precise prognosis of cancer. Furthermore, there has been a demand for a rapid and convenient method for precise prognosis of cancer.

Means for Solving the Invention

The present inventors have found that methylated DNA can be detected rapidly and conveniently by amplifying bisulfite-treated DNA by PCR and separating the obtained PCR amplification product by ion exchange chromatography. The present inventors have further found that a signal pattern obtained by ion exchange chromatography differs between DNA obtained from CIMP-positive cancer and DNA obtained from CIMP-negative cancer, and cancer having poor prognosis can be determined by analyzing the difference in the pattern. On the basis of these findings, the present invention has been completed.

The present invention provides the followings:

[1] A method for determining a tissue having renal cell carcinoma, comprising:
(1) treating genomic DNA prepared from a renal tissue of a subject with bisulfite;
(2) amplifying the bisulfite-treated DNA by PCR;
(3) subjecting the obtained PCR amplification product to ion exchange chromatography;
(4) obtaining the retention time of a detection signal obtained by the chromatography; and
(5) determining the tissue as a tissue having renal cell carcinoma obtained from a renal cell carcinoma patient with poor prognosis when the result of the step (4) is shorter than a retention time serving as a reference.

[2] A method for obtaining data for determining a tissue having renal cell carcinoma, comprising:
(1) treating genomic DNA prepared from a renal tissue of a subject with bisulfite;
(2) amplifying the bisulfite-treated DNA by PCR;
(3) subjecting the obtained PCR amplification product to ion exchange chromatography;
(4) obtaining the retention time of a detection signal obtained by the chromatography; and
(5) obtaining whether or not the result of the step (4) is shorter than a retention time serving as a reference as data for determining whether or not the tissue is a tissue having renal cell carcinoma obtained from a renal cell carcinoma patient with poor prognosis.

[3] A method for determining the prognosis of a renal cell carcinoma patient, comprising:
(1) treating genomic DNA prepared from a renal tissue of a subject with bisulfite;
(2) amplifying the bisulfite-treated DNA by PCR;
(3) subjecting the obtained PCR amplification product to ion exchange chromatography;
(4) obtaining the retention time of a detection signal obtained by the chromatography; and
(5) determining the renal cell carcinoma of the subject as having poor prognosis when the result of the step (4) is shorter than a retention time serving as a reference.

[4] The method according to any one of [1] to [3], wherein the DNA to be amplified by PCR in the step (2) comprises a CpG island in at least one gene selected from the group consisting of FAM150A, GRM6, ZNF540, ZFP42, ZNF154, RIMS4, PCDHAC1, KHDRBS2, ASCL2, KCNQ1, PRAC, WNT3A, TRH, FAM78A, ZNF671, SLC13A5, and NKX6-2.

[5] The method according to any one of [1] to [3], wherein the DNA to be amplified by PCR in the step (2) comprises a FAM150A gene promoter region.

[6] The method according to any one of [1] to [3], wherein the PCR in the step (2) employs PCR primers represented by SEQ ID NOs: 51 and 52.

[7] The method according to any one of [1] to [6], further comprising, before the step (4) s:
(1') treating unmethylated DNA corresponding to the PCR amplification region of the genomic DNA prepared from a renal tissue of a subject with bisulfite;
(2') amplifying the bisulfite-treated DNA obtained in the step (1') by PCR;
(3') subjecting the PCR amplification product obtained in the step (2') to ion exchange chromatography; and (3a) obtaining difference data by subtracting a detection signal obtained by the chromatography in the step (3') from a detection signal obtained by the chromatography in the step (3).

Effects of the Invention

The present invention provides a rapid, convenient, and highly accurate method for determining the prognosis of cancer. According to the present invention, a risk of recurrence in cancer patients can be determined more rapidly, conveniently, and highly accurately. Therefore, the present invention enables early resumption of treatment to cancer patients who are in need of treatment. Thus, the present invention contributes to improvement in the survival rate of cancer patients.

BRIEF DESCRIPTION OF THE DRAWINGS

FIG. 1A is chromatograms of DNAs differing in DNA methylation rate (0%, 25%, 50%, 75%, and 100%). FIG. 1B is chromatograms of 50% methylated DNAs differing in DNA methylation position (random, closer to the 5' end, closer to the 3' end, and center).

FIGS. 3A and 3B show the results about the CIMP-positive samples. FIGS. 3C and 3D show the results about the CIMP-negative samples.

FIG. 5-1 shows results of comparing DNA methylation rates obtained in the MassARRAY method and the method of the present invention.

FIG. 5-2 shows results of comparing DNA methylation rates obtained in the MassARRAY method and the method of the present invention.

EMBODIMENTS FOR CARRYING OUT THE INVENTION

Figure 1:
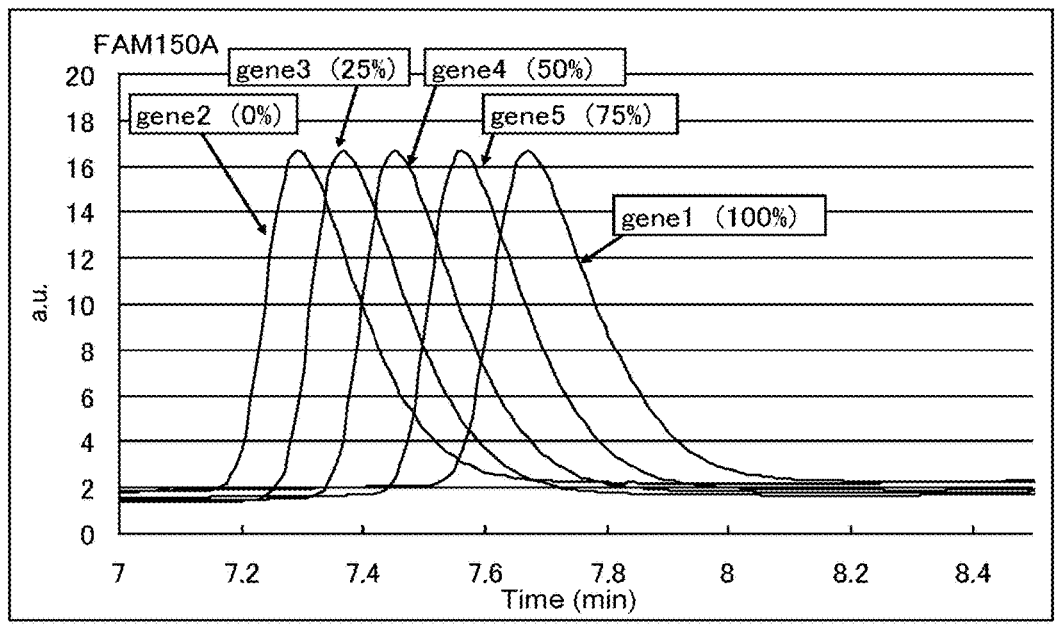
FIG. 1 shows variation in chromatography elution time caused by DNA methylation rates.
Figure 1:
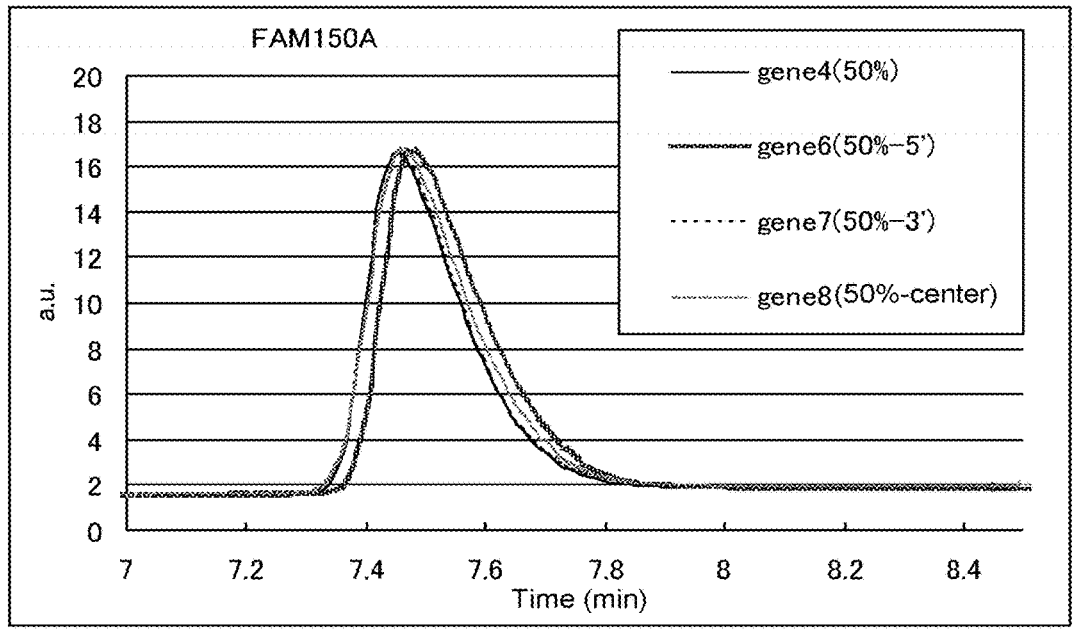

In the present specification, the "renal cell carcinoma" is a cancer which develops by the malignant transformation of tubular epithelial cells of the kidney and is classified from its pathological features into clear cell type, granular cell type, chromophobe type, spindle type, cyst-associated type, type originating in cyst, cystic type, and papillary type. In the present specification, examples of the "subject" include patients affected by renal cell carcinoma, patients suspected of having renal cell carcinoma, and patients whose renal cell carcinoma has been treated by surgical operation or the like.

In the present specification, examples of the "poor prognosis" of cancer include low prognostic (postoperative) survival rates of subjects and more specifically include a postoperative recurrence-free survival rate (tumor-free survival rate) of 50% or lower after a lapse of 500 days or a postoperative overall survival rate of 70% or lower after a lapse of 1,500 days.

In the present specification, the "DNA methylation" means a state where carbon at position 5 of cytosine in DNA is methylated. In the present specification, the phrase "detecting methylation" of DNA means to measure the presence or absence, abundance, or abundance ratio of methylated DNA in this DNA, or the methylation rate of this DNA. In the present specification, the "DNA methylation rate" means the proportion of methylated cytosine of a CpG island in particular DNA to be detected and can be indicated by, for example, the ratio of the number of methylated cytosine to the total number of cytosine (methylated cytosine and unmethylated cytosine) in the CpG island of the particular DNA to be detected.

In the present specification, the "CpG site" means a site where a phosphodiester bond (p) is formed between cytosine (C) and guanine (G) in DNA. In the present specification, the CpG island refers to a region in which a two-nucleotide sequence of cytosine (C)-guanine (G) via a phosphodiester bond (p) appears with high frequency. The CpG island often resides in a promoter region upstream of a gene. In the present specification, the "CpG site or CpG island of (a) gene" means a CpG island located at a position close to the coding region of the gene, or a CpG site contained in the CpG island, and preferably means a CpG site or a CpG island present in the promoter region of the gene. The CpG site or the CpG island of a particular gene can be identified on the basis of a method such as MassARRAY method or pyrosequencing.

In the present specification, the "retention time serving as a reference" (hereinafter, also referred to as a reference retention time) refers to a HPLC retention time which can differentiate between a CIMP-positive group and a CIMP-negative group, or a HPLC retention time which can differentiate between a signal group derived from highly methylated DNA and a signal group derived from DNA having a low degree of methylation as to detection signals derived from genomic DNA prepared from renal cell carcinoma. Specifically, since a signal derived from highly methylated DNA is detected at a retention time shorter than the retention time serving as a reference (reference retention time), a specimen having a detection signal at a retention time shorter than the reference retention time can be determined as having poor prognosis. The reference retention time mentioned above can be set to a reference retention time appropriate for HPLC analysis conditions, a region of genomic DNA, or the type of a gene marker, etc., because a chromatogram varies depending on these conditions, etc. It is also preferred to set the reference retention time in consideration of necessary clinical sensitivity.

In one embodiment, the present invention provides a method for determining a tissue having renal cell carcinoma, comprising:

(1) treating genomic DNA prepared from a renal tissue of a subject with bisulfite;

(2) amplifying the bisulfite-treated DNA by PCR;

(3) subjecting the obtained PCR amplification product to ion exchange chromatography;

(4) obtaining the retention time of a detection signal obtained by the chromatography; and (5) determining the tissue as a tissue having renal cell carcinoma obtained from a renal cell carcinoma patient with poor prognosis when the result of the step (4) is shorter than a retention time serving as a reference.

In another embodiment, the present invention provides a method for obtaining data for determining a tissue having renal cell carcinoma, comprising:

(1) treating genomic DNA prepared from a renal tissue of a subject with bisulfite;

(2) amplifying the bisulfite-treated DNA by PCR;

(3) subjecting the obtained PCR amplification product to ion exchange chromatography;

(4) obtaining the retention time of a detection signal obtained by the chromatography; and (5) obtaining whether or not the result of the step (4) is shorter than a retention time serving as a reference as data for determining whether or not the tissue is a tissue having renal cell carcinoma obtained from a renal cell carcinoma patient with poor prognosis.

In an alternative embodiment, the present invention provides a method for determining the prognosis of a renal cell carcinoma patient, comprising:

(1) treating genomic DNA prepared from a renal tissue of a subject with bisulfite;

(2) amplifying the bisulfite-treated DNA by PCR;

(3) subjecting the obtained PCR amplification product to ion exchange chromatography;

(4) obtaining the retention time of a detection signal obtained by the chromatography; and (5) determining the renal cell carcinoma of the subject as having poor prognosis when the result of the step (4) is shorter than a retention time serving as a reference.

In a further alternative embodiment, the present invention provides a method for determining a tissue having renal cell carcinoma or a renal cell carcinoma patient, further comprising, before the step (4):

(1') treating unmethylated DNA corresponding to the PCR amplification region of the genomic DNA prepared from a renal tissue of a subject with bisulfite;

(2') amplifying the bisulfite-treated DNA obtained in the step (1') by PCR;

(3') subjecting the PCR amplification product obtained in the step (2') to ion exchange chromatography; and (3a) obtaining difference data by subtracting a detection signal obtained by the chromatography in the step (3') from a detection signal obtained by the chromatography in the step (3).

The renal tissue of a subject can be a renal tissue containing DNA or a cell thereof. Examples thereof include tissues collected by biopsy, surgical operation, or the like, and frozen products or fixed preparations thereof. It is desirable to use a frozen renal tissue from the viewpoint of suppressing the degradation, etc. of genomic DNA and more efficiently detecting DNA methylation.

The method for preparing sample DNA from the renal tissue or the cell is not particularly limited, and an approach known in the art can be appropriately selected for use. Examples of the method known in the art for preparing DNA include phenol-chloroform method, and DNA extraction method as mentioned later using a commercially available DNA extraction kit, for example, QIAamp DNA Mini kit (manufactured by Qiagen N.V.), Clean Columns (manufactured by Hermes-NexTec GmbH), AquaPure (manufactured by Bio-Rad Laboratories, Inc.), ZR Plant/Seed DNA Kit (manufactured by Zymo Research Corp.), prepGEM (manufactured by ZyGEM NZ, Ltd.), or BuccalQuick (manufactured by TrimGen Corp.).

Subsequently, the extracted sample DNA is treated with bisulfite. The method for treating the DNA with bisulfite is not particularly limited, and an approach known in the art can be appropriately selected for use. Examples of the method known in the art for bisulfite treatment include methods as mentioned above using a commercially available kit, for example, EpiTect Bisulfite Kit (48) (manufactured by Qiagen N.V.), MethylEasy (manufactured by Human Genetic Signatures Pty), Cells-to-CpG Bisulfite Conversion Kit (manufactured by Applied Biosystems, Inc.), or CpGenome Turbo Bisulfite Modification Kit (manufactured by Merck Millipore).

Subsequently, the bisulfite-treated sample DNA is amplified by PCR. The PCR amplification method is not particularly limited, and an approach known in the art can be appropriately selected for use according to the sequence, length, amount, etc. of the DNA to be amplified.

As for renal cell carcinoma, it has been reported that DNA methylation in 17 genes (FAM150A, GRM6, ZNF540, ZFP42, ZNF154, RIMS4, PCDHAC1, KHDRBS2, ASCL2, KCNQ1, PRAC, WNT3A, TRH, FAM78A, ZNF671, SLC13A5, and NKX6-2) is associated with the poor prognosis (CIMP-positive) of renal cell carcinoma (Patent Literature 4). Thus, in the method of the present invention, the target DNA to be amplified by PCR is preferably selected such that the DNA methylation of a CpG island in at least one gene selected from the group consisting of these 17 genes can be detected, and more preferably selected such that the methylation of the CpG sites of these 17 genes can be detected. For example, the target DNA is DNA encoding a portion or the whole of the coding region and/or the promoter region of any of the 17 genes. The target DNA is preferably DNA encoding a portion or the whole of the promoter region of any of the 17 genes, more preferably DNA encoding a portion or the whole of the CpG island of any of the 17 genes.

FAM150A is a gene encoding a protein specified by RefSeq ID: NP_997296; GRM6 is a gene encoding a protein specified by RefSeq ID: NP_000834; ZNF540 is a gene encoding a protein specified by RefSeq ID: NP_689819; ZFP42 is a gene encoding a protein specified by RefSeq ID: NP_777560; ZNF154 is a gene encoding a protein specified by RefSeq ID: NP_001078853; RIMS4 is a gene encoding a protein specified by RefSeq ID: NP_892015; PCDHAC1 is a gene encoding a protein specified by RefSeq ID: NP_061721; KHDRBS2 is a gene encoding a protein specified by RefSeq ID: NP_689901; ASCL2 is a gene encoding a protein specified by RefSeq ID: NP_005161; KCNQ1 is a gene encoding a protein specified by RefSeq ID: NP_000209; PRAC is a gene encoding a protein specified by RefSeq ID: NP_115767; WNT3A is a gene encoding a protein specified by RefSeq ID: NP_149122; TRH is a gene encoding a protein specified by RefSeq ID: NP_009048; FAM78A is a gene encoding a protein specified by RefSeq ID: NP_203745; ZNF671 is a gene encoding a protein specified by RefSeq ID: NP_079109; SLC13A5 is a gene encoding a protein specified by RefSeq ID: NP_808218; and NKX6-2 is a gene encoding a protein specified by RefSeq ID: NP_796374.

The CpG sites of the 17 genes are located at positions on the chromosomes described in Tables 1 to 4 on the basis of positions on the NCBI database Genome Build 37, which is a reference human genomic sequence.

TABLE 1

| Gene symbol | Chromosome number | Position on chromosome |
| --- | --- | --- |
| FAM150A | 8 | 53478309 |
| | | 53478316, 53478323 |
| | | 53478361, 53478363, 53478366 |
| | | 53478396, 53478403 |
| | | 53478426, 53478428 |
| | | 53478454 |
| | | 53478477 |
| | | 53478496, 53478499 |
| | | 53478504 |
| | | 53478511 |
| | | 53478536 |
| | | 53478585, 53478588, 53478592 |
| | | 53478624, 53478626 |

TABLE 1-continued

| Gene symbol | Chromosome number | Position on chromosome |
|---|---|---|
| GRM6 | 5 | 178422244 |
|  |  | 178422320, 178422324 |
|  |  | 178422375, 178422380 |
| ZNF540 | 19 | 38042472, 38042474 |
|  |  | 38042496 |
|  |  | 38042518 |
|  |  | 38042530, 38042532 |
|  |  | 38042544, 38042552 |
|  |  | 38042576 |
|  |  | 38042800, 38042802 |
|  |  | 38042816 |

TABLE 2

| Gene symbol | Chromosome number | Position on chromosome |
|---|---|---|
| ZFP42 | 4 | 188916867 |
|  |  | 188916875 |
|  |  | 188916899 |
|  |  | 188916913 |
|  |  | 188916982, 188916984 |
| ZNF154 | 19 | 58220494 |
|  |  | 58220567 |
|  |  | 58220627 |
|  |  | 58220657, 58220662 |
|  |  | 58220706 |
|  |  | 58220766, 58220773 |
| RIMS4 | 20 | 43438576 |
|  |  | 43438621 |
|  |  | 43438865 |
| PCDHAC1 | 5 | 140306458 |
| KHDRBS2 | 6 | 62995963 |
| ASCL2 | 11 | 2292004 |
|  |  | 2292542, 2292544 |
| KCNQ1 | 11 | 2466409 |
| PRAC | 17 | 46799640 |
|  |  | 46799645, 46799648 |
|  |  | 46799654 |
|  |  | 46799745 |
|  |  | 46799755 |

TABLE 3

| Gene symbol | Chromosome number | Position on chromosome |
|---|---|---|
| WNT3A | 1 | 228194448 |
|  |  | 228195688 |
|  |  | 228195722 |
|  |  | 228195779 |
| TRH | 3 | 129693350, 129693352, |
|  |  | 129693355, 129693358 |
|  |  | 129693406, 129693412 |
|  |  | 129693425 |
|  |  | 129693500 |
|  |  | 129693518, 129693521, |
|  |  | 129693528 |
|  |  | 129693540, 129693543 |
|  |  | 129693563 |
|  |  | 129693570, 129693574 |
|  |  | 129693586 |
|  |  | 129693607 |
|  |  | 129693613 |
|  |  | 129693628 |
|  |  | 129693635 |
|  |  | 129693672 |
| FAM78A | 9 | 134152531 |
| ZNF671 | 19 | 58238740 |
|  |  | 58238780 |
|  |  | 58238810 |
|  |  | 58238850 |
|  |  | 58238928 |
|  |  | 58238954 |
|  |  | 58238987 |
|  |  | 58239012 |
|  |  | 58239027 |

TABLE 4

| Gene symbol | Chromosome number | Position on chromosome |
|---|---|---|
| SLC13A5 | 17 | 6616653, 6616655, 6616657 |
|  |  | 6616702, 6616705, 6616707 |
|  |  | 6616733 |
|  |  | 6616751 |
|  |  | 6616763, 6616768 |
|  |  | 6616812 |
|  |  | 6616826, 6616828 |
|  |  | 6616851, 6616854, 6616857 |
|  |  | 6616927, 6616929 |
|  |  | 6616968, 6616973 |
|  |  | 6617030, 6617038, 6617040, |
|  |  | 6617044 |
|  |  | 6617077 |
|  |  | 6617124 |
|  |  | 6617251, 6617255 |
|  |  | 6617287, 6617291 |
|  |  | 6617300, 6617305 |
|  |  | 6617382 |
|  |  | 6617421, 6617423 |
|  |  | 6617456 |
|  |  | 6617466, 6617470 |
|  |  | 6617382 |
|  |  | 6617398, 6617402, 6617405 |
|  |  | 6617415 |
|  |  | 6617421, 6617423 |
|  |  | 6617466, 6617470 |
|  |  | 6617595, 6617597 |
| NKX6-2 | 10 | 134599860 |

In the CIMP determination described in Patent Literature 4, the CpG site whose DNA methylation is to be detected is preferably at least one CpG site selected from the group consisting of chromosome 8 position 53,478,454, chromosome 5 position 178,422,244, chromosome 19 position 38,042,472, chromosome 4 position 188,916,867, chromosome 19 position 58,220,662, chromosome 20 position 43,438,865, chromosome 5 position 140,306,458, chromosome 6 position 62,995,963, chromosome 11 position 2,292,004, chromosome 11 position 2,466,409, chromosome 17 position 46,799,640, chromosome 19 position 58,220,494, chromosome 1 position 228,194,448, chromosome 3 position 129,693,613, chromosome 9 position 134,152,531, chromosome 19 position 58,238,928, chromosome 17 position 6,617,030, and chromosome 10 position 134,599,860 as positions on the NCBI database Genome Build 37, which is a reference human genomic sequence.

The chain length of the PCR amplification product can be appropriately selected in consideration of factors such as reduction in PCR amplification time and reduction in analysis time in ion exchange chromatography, and maintenance of separation performance. In the case of using, for example, sample DNA rich in CpG islands, the chain length of the PCR amplification product is preferably 1,000 bp or shorter, more preferably 700 bp or shorter, further preferably 500 bp or shorter. On the other hand, in the case of using sample DNA having a few CpG islands, the chain length of the PCR amplification product is 30 to 40 bp as the lower limit, which is the chain length of a PCR amplification product obtained using primers of approximately 15 mer in order to avoid nonspecific hybridization in PCR. Meanwhile, it is preferred to design primers such that the content of CpG islands is large. For example, cytosine of CpG sites is preferably contained at 2% or more, more preferably 5% or more, with respect to the chain length of the PCR amplification product.

Subsequently, the obtained PCR amplification product is subjected to ion exchange chromatography. The ion exchange chromatography according to the present invention is preferably anion exchange chromatography. The column packing material for use in the ion exchange chromatography according to the present invention is not particularly limited as long as the packing material is substrate particles having a strong cationic group on the surface. Substrate particles having both a strong cationic group and a weak cationic group on the surface of the packing material as shown in Patent Literature 2 are preferred.

In the present specification, the strong cationic group means a cationic group which is dissociated in a wide pH range of from 1 to 14. Specifically, the strong cationic group can maintain its dissociated (cationized) state without being influenced by the pH of an aqueous solution.

Examples of the strong cationic group include quaternary ammonium groups. Specific examples thereof include trialkylammonium groups such as a trimethylammonium group, a triethylammonium group, and a dimethylethylammonium group. Examples of the counter ion for the strong cationic group include halide ions such as a chloride ion, a bromide ion, and an iodide ion.

The amount of the strong cationic group introduced to the surface of the substrate particles is not particularly limited and is preferably 1 µeq/g as the lower limit and 500 µeq/g as the upper limit with respect to the dry weight of the packing material. If the amount of the strong cationic group is less than 1 µeq/g, separation performance may be deteriorated due to weak retention strength. If the amount of the strong cationic group exceeds 500 µeq/g, retention strength may be too strong to easily elute the PCR amplification product, resulting in problems such as too long an analysis time.

In the present specification, the weak cationic group means a cationic group having pka of 8 or higher. Specifically, the weak cationic group changes its dissociated state by the influence of the pH of an aqueous solution. Specifically, at pH higher than 8, the proton of the weak cationic group is dissociated so that the ratio of a group having no positive charge is increased. On the other hand, at pH lower than 8, the weak cationic group is protonated so that the ratio of a group having positive charge is increased.

Examples of the weak cationic group include tertiary amino groups, secondary amino groups, and primary amino groups. Among them, a tertiary amino group is desirable.

The amount of the weak cationic group introduced to the surface of the substrate particles is not particularly limited and is preferably 0.5 µeq/g as the lower limit and 500 µeq/g as the upper limit with respect to the dry weight of the packing material. If the amount of the weak cationic group is less than 0.5 µeq/g, separation performance may not be improved due to too small an amount. If the amount of the weak cationic group exceeds 500 µeq/g, retention strength may be too strong to easily elute the PCR amplification product, resulting in problems such as too long an analysis time, as with the strong cationic group.

The amount of the strong cationic group or the weak cationic group on the surface of the substrate particles can be measured by quantifying a nitrogen atom contained in an amino group. Examples of the method for quantifying nitrogen include Kjeldahl method. In the case of the packing material described in the present invention (Examples), first, nitrogen contained in the strong cationic group after polymerization is quantified. Subsequently, nitrogen contained in the strong cationic group and the weak cationic group after introduction of the weak cationic group is quantified. As a result, the amount of the weak cationic group introduced later can be calculated. Such quantification allows the amount of the strong cationic group and the amount of the weak cationic group to be adjusted within the ranges described above for preparing the packing material.

For example, synthetic polymer fine particles obtained using polymerizable monomers or the like, or inorganic fine particles such as fine silica particles can be used as the substrate particles. Hydrophobic cross-linked polymer particles consisting of a synthetic organic polymer are desirable.

The hydrophobic cross-linked polymer may be any of a hydrophobic cross-linked polymer obtained by copolymerizing at least one hydrophobic cross-linkable monomer and at least one monomer having a reactive functional group, and a hydrophobic cross-linked polymer obtained by copolymerizing at least one hydrophobic cross-linkable monomer, at least one monomer having a reactive functional group, and at least one hydrophobic cross-linkable monomer.

The hydrophobic cross-linkable monomer is not particularly limited as long as the monomer has two or more vinyl groups in one molecule. Examples thereof include: di(meth)acrylic acid esters such as ethylene glycol di(meth)acrylate, polyethylene glycol di(meth)acrylate, propylene glycol di(meth)acrylate, and polypropylene glycol di(meth)acrylate; tri(meth)acrylic acid esters such as trimethylol methane tri(meth)acrylate and tetramethylol methane tri(meth)acrylate; tetra(meth)acrylic acid esters; and aromatic compounds such as divinylbenzene, divinyltoluene, divinylxylene, and divinylnaphthalene. In the present specification, the (meth)acrylate means acrylate or methacrylate, and (meth)acryl means acryl or methacryl.

Examples of the monomer having a reactive functional group include glycidyl (meth)acrylate and isocyanatoethyl (meth)acrylate.

The hydrophobic non-cross-linkable monomer is not particularly limited as long as the monomer is a non-cross-linkable polymerizable organic monomer having hydrophobic properties. Examples thereof include: (meth)acrylic acid esters such as methyl (meth)acrylate, ethyl (meth)acrylate, butyl (meth)acrylate, and t-butyl (meth)acrylate; and styrene monomers such as styrene and methylstyrene.

When the hydrophobic cross-linked polymer is obtained by copolymerizing the hydrophobic cross-linkable monomer and the monomer having a reactive functional group, the content ratio of a segment derived from the hydrophobic cross-linkable monomer in the hydrophobic cross-linked polymer is preferably 10 wt % as the lower limit, more preferably 20 wt % as the lower limit.

The packing material for the ion exchange chromatography of the present invention preferably has a polymer layer having the strong cationic group and the weak cationic group on the surface of the substrate particles. For the polymer having the strong cationic group and the weak cationic group, it is preferred that the strong cationic group and the weak cationic group should be respectively derived from independent monomers. Specifically, the packing material for the ion exchange chromatography of the present invention is preferably a packing material in which the weak cationic group is introduced in the surface of coated polymer particles consisting of the hydrophobic cross-linked polymer particles and a layer of a hydrophilic polymer having the strong cationic group copolymerized at the surface of the hydrophobic cross-linked polymer particles.

The hydrophilic polymer having the strong cationic group is formed from hydrophilic monomers having the strong cationic group and can contain a segment derived from one or more hydrophilic monomers having the strong cationic group. Specifically, examples of the method for producing the hydrophilic polymer having the strong cationic group include a method which involves homopolymerizing a hydrophilic monomer having the strong cationic group, a method which involves copolymerizing two or more hydrophilic monomers each having the strong cationic group, and a method which involves copolymerizing a hydrophilic monomer having the strong cationic group and a hydrophilic monomer having no strong cationic group.

The hydrophilic monomer having the strong cationic group preferably has a quaternary ammonium group. Specific examples thereof include ethyl methacrylate triethylammonium chloride, ethyl methacrylate dimethylethylammonium chloride, ethyl methacrylate dimethylbenzylammonium chloride, ethyl acrylate dimethylbenzylammonium chloride, ethyl acrylate triethylammonium chloride, ethyl acrylate dimethylethylammonium chloride, acrylamide ethyltrimethylammonium chloride, acrylamide ethyltriethylammonium chloride, and acrylamide ethyl dimethylethylammonium chloride.

A method known in the art can be used as a method for introducing the weak cationic group to the surface of the coated polymer particles. Specifically, examples of the method for introducing a tertiary amino group as the weak cationic group include: a method which involves copolymerizing the hydrophilic monomer having the strong cationic group at the surface of the hydrophobic cross-linked polymer particles consisting of a hydrophobic cross-linked polymer having a segment derived from a monomer having a glycidyl group, and subsequently reacting the glycidyl group with a reagent having a tertiary amino group; a method which involves copolymerizing the hydrophilic monomer having the strong cationic group at the surface of the hydrophobic cross-linked polymer particles consisting of a hydrophobic cross-linked polymer having a segment derived from a monomer having an isocyanate group, and subsequently reacting the isocyanate group with a reagent having a tertiary amino group; a method which involves copolymerizing the hydrophilic monomer having the strong cationic group and a monomer having a tertiary amino group at the surface of the hydrophobic cross-linked polymer particles; a method which involves introducing a tertiary amino group to the surface of the coated polymer particles having a hydrophilic polymer layer having the strong cationic group using a silane coupling agent having the tertiary amino group; a method which involves copolymerizing the hydrophilic monomer having the strong cationic group at the surface of the hydrophobic cross-linked polymer particles consisting of a hydrophobic cross-linked polymer having a segment derived from a monomer having a carboxy group, and subsequently condensing the carboxy group with a reagent having a tertiary amino group using carbodiimide; and a method which involves copolymerizing the hydrophilic monomer having the strong cationic group at the surface of the hydrophobic cross-linked polymer particles consisting of a hydrophobic cross-linked polymer having a segment derived from a monomer having an ester bond, hydrolyzing the ester bond moiety, and then condensing a carboxy group formed by the hydrolysis with a reagent having a tertiary amino group using carbodiimide. Among them, the method which involves copolymerizing the hydrophilic monomer having the strong cationic group at the surface of the hydrophobic cross-linked polymer particles consisting of a hydrophobic cross-linked polymer having a segment derived from a monomer having a glycidyl group, and subsequently reacting the glycidyl group with a reagent having a tertiary amino group, or the method which involves copolymerizing the hydrophilic monomer having the strong cationic group at the surface of the hydrophobic cross-linked polymer particles consisting of a hydrophobic cross-linked polymer having a segment derived from a monomer having an isocyanate group, and subsequently reacting the isocyanate group with a reagent having a tertiary amino group, is preferred.

The reagent having a tertiary amino group which is reacted with the reactive functional group such as a glycidyl group or an isocyanate group is not particularly limited as long as the reagent has a functional group reactable with the tertiary amino group and the reactive functional group. Examples of the functional group reactable with the tertiary amino group and the reactive functional group include primary amino groups and a hydroxy group. Among others, a group having a terminal primary amino group is preferred. Specific examples of the reagent having the functional group include N,N-dimethylaminomethylamine, N,N-dimethylaminoethylamine, N,N-dimethylaminopropylamine, N,N-dimethylaminobutylamine, N,N-diethylaminoethylamine, N,N-diethylaminopropylethylamine, N,N-diethylaminobutylamine, N,N-diethylaminopentylamine, N,N-diethylaminohexylamine, N,N-dipropylaminobutylamine, and N,N-dibutylaminopropylamine.

For the relative positional relationship between the strong cationic group (preferably, a quaternary ammonium salt) and the weak cationic group (preferably, a tertiary amino group), it is preferred that the strong cationic group should be positioned more distant than the weak cationic group from the surface of the substrate particles, i.e., positioned on the outer side of the weak cationic group. Preferably, for example, the weak cationic group is located within 30 angstroms from the surface of the substrate particles, and the strong cationic group is located within 300 angstroms from the surface of the substrate particles and on the outer side of the weak cationic group.

The average particle size of the substrate particles which are used as the packing material for the ion exchange chromatography of the present invention is not particularly limited and is preferably 0.1 µm as the lower limit and 20 µm as the upper limit. If the average particle size is less than 0.1 µm, poor separation may occur due to too high an intra-column pressure. If the average particle size exceeds 20 µm, poor separation may occur due to too large an intra-column dead volume. In the present specification, the average particle size refers to a volume-average particle size and can be measured using a particle size distribution measurement apparatus (e.g., AccuSizer 780, manufactured by Particle Sizing Systems).

Conditions known in the art can be used for the composition of an eluent for use in the ion exchange chromatography according to the present invention.

The buffer solution for use in the eluent is preferably a buffer solution containing a salt compound known in the art, or an organic solvent. Specific examples thereof include a tris-HCl buffer solution, a TE buffer solution consisting of tris and EDTA, and a TBA buffer solution consisting of tris, boric acid, and EDTA.

The pH of the eluent is not particularly limited and is preferably 5 as the lower limit and 10 as the upper limit. At the pH set to within this range, the weak cationic group is considered to also work effectively as an ion exchange group (anion exchange group). The pH of the eluent is more preferably 6 as the lower limit and 9 as the upper limit.

Examples of the salt contained in the eluent include: salts consisting of a halide and an alkali metal, such as sodium chloride, potassium chloride, sodium bromide, and potassium bromide; and salts consisting of a halide and an alkaline earth metal, such as calcium chloride, calcium bromide, magnesium chloride, and magnesium bromide; and inorganic acid salts such as sodium perchlorate, potassium perchlorate, sodium sulfate, potassium sulfate, ammonium sulfate, sodium nitrate, and potassium nitrate. Alternatively, an organic acid salt such as sodium acetate, potassium acetate, sodium succinate, or potassium succinate may be used. Any one of these salts may be used alone or, two or more thereof may be used in combination.

The salt concentration of the eluent can be appropriately adjusted according to analysis conditions and is preferably 10 mmol/L as the lower limit and 2,000 mmol/L as the upper limit, more preferably 100 mmol/L as the lower limit and 1,500 mmol/L as the upper limit.

The eluent for use in the ion exchange chromatography of the present invention further contains an anti-chaotropic ion for further enhancing separation performance. The anti-chaotropic ion has properties opposite to those of a chaotropic ion and works to stabilize a hydrated structure. Therefore, the anti-chaotropic ion is effective for strengthening the hydrophobic interaction between the packing material and a nucleic acid molecule. The main interaction of the ion exchange chromatography of the present invention is electrostatic interaction. Separation performance is enhanced through the use of the work of the hydrophobic interaction in addition thereto.

Examples of the anti-chaotropic ion contained in the eluent include a phosphate ion ($PO_4^{3-}$), a sulfate ion ($SO_4^{2-}$), an ammonium ion ($NH_4^+$), a potassium ion ($K^+$), and a sodium ion ($Na^+$). Among combinations of these ions, a sulfate ion and an ammonium ion are preferably used. Any one of these anti-chaotropic ions may be used alone, or two or more thereof may be used in combination. Some of the anti-chaotropic ions mentioned above comprise a salt contained in the eluent or a component of the buffer solution. Use of such a component is suitable for the present invention, because the component possesses both of properties or buffering ability as the salt contained in the eluent and properties as the anti-chaotropic ion.

The concentration at the time of analysis of the anti-chaotropic ion in the eluent for the ion exchange chromatography of the present invention can be appropriately adjusted according to an analyte and is desirably 2,000 mmol/L or lower in terms of anti-chaotropic salt. Specific examples of such a method can include a method which involves performing gradient elution at anti-chaotropic salt concentrations ranging from 0 to 2,000 mmol/L. Thus, the concentration of the anti-chaotropic salt at the start of analysis does not have to be 0 mmol/L, and the concentration of the anti-chaotropic salt at the completion of analysis does not have to be 2,000 mmol/L. The gradient elution method may be a low-pressure gradient method or may be a high-pressure gradient method. The method preferably involves performing elution while the concentration is precisely adjusted by the high-pressure gradient method.

The anti-chaotropic ion may be added to only one eluent for use in elution or may be added to a plurality of eluents. Also, the anti-chaotropic ion may play a role both in the effect of enhancing the hydrophobic interaction between the packing material and the PCR amplification product or the buffering ability and in the effect of eluting the PCR amplification product from the column.

The column temperature for analyzing the PCR amplification product by the ion exchange chromatography according to the present invention is preferably 30° C. or higher, more preferably 40° C. or higher, further preferably 45° C. or higher. If the column temperature in the ion exchange chromatography is lower than 30° C., the hydrophobic interaction between the packing material and the PCR amplification product is weakened, and the desired separating effect is difficult to obtain. If the column temperature in the ion exchange chromatography is lower than 45° C., the PCR amplification product of bisulfite-treated methylated DNA (methylated DNA sample) and the PCR amplification product of bisulfite-treated unmethylated DNA (unmethylated DNA sample) do not much differ in retention time. When the column temperature is 60° C. or higher, the methylated DNA sample and the unmethylated DNA sample differ more largely in retention time and respectively exhibit more clear peaks. Therefore, DNA methylation can be detected more accurately.

As the column temperature in the ion exchange chromatography is higher, the methylated DNA sample and the unmethylated DNA sample are more clearly separable. Therefore, the methylated DNA and the unmethylated DNA tend to differ in their peak areas or peak heights at retention times according to their abundance ratios in the sample DNA. Thus, at a higher column temperature, the respective abundances or abundance ratios of the methylated DNA and the unmethylated DNA in the sample DNA can be measured more easily on the basis of the difference between the peak areas or heights at retention times of the methylated DNA sample and the unmethylated DNA sample.

On the other hand, a column temperature of 90° C. or higher in the ion exchange chromatography is not preferred for the analysis because two strands of the nucleic acid molecule in the PCR amplification product are dissociated. A column temperature of 100° C. or higher is not preferred for the analysis because the eluent might be boiled. Thus, the column temperature for analyzing the PCR amplification product by the ion exchange chromatography according to the present invention can be 30° C. or higher and lower than 90° C. and is preferably 40° C. or higher and lower than 90° C., more preferably 45° C. or higher and lower than 90° C., further preferably 55° C. or higher and lower than 90° C., still further preferably 55° C. or higher and 85° C. or lower, particularly preferably 60° C. or higher and 85° C. or lower.

The sample injection volume to the ion exchange chromatography column is not particularly limited and can be appropriately adjusted according to the ion exchange capacity of the column and the sample concentration. The flow rate is preferably from 0.1 mL/min to 3.0 mL/min, more preferably from 0.5 mL/min to 1.5 mL/min. At a slower flow rate, improved separation can be expected. Too slow a flow rate might require a long time for analysis or incur reduction in separation performance due to broader peaks. On the other hand, a faster flow rate is advantageous in terms of reduction in analysis time, but incurs reduction in separation performance due to peak compression. Accordingly, it is desirable to set the flow rate to within the range described above, though this parameter is appropriately adjusted according to the performance of the column. The retention time of each sample can be predetermined by a preliminary experiment on each sample. A flowing method known in the art, such as linear gradient elution method or stepwise elution method can be used. The flowing method according to the present invention is preferably linear gradient elution method. The amplitude of the gradient can be appropriately adjusted within a range of the eluent for use in elution from 0% to 100% according to the separation performance of the column and the characteristics of the analyte (here, the PCR amplification product).

In the present invention, the PCR amplification product of the bisulfite-treated DNA is subjected to ion exchange chromatography by the procedures described above to detect DNA methylation in the sample DNA.

The treatment of DNA with bisulfite converts unmethylated cytosine in the DNA to uracil, while leaving methylated cytosine unaltered. The PCR amplification of the bisulfite-treated DNA further replaces uracil derived from the unmethylated cytosine with thymine and therefore results in the difference in the abundance ratios of cytosine and thymine between methylated DNA and unmethylated DNA. Thus, DNA in the PCR amplification product has a distinctive sequence according to its methylation rate. The PCR amplification product is subjected to ion exchange chromatography to obtain a chromatogram showing a distinctive signal according to the nucleotide sequence of DNA contained in the amplification product.

The presence or absence of methylated DNA in sample DNA can be measured, for example, by comparing a detection signal from the PCR amplification product of the bisulfite-treated sample DNA with a detection signal from the PCR amplification product of bisulfite-treated DNA having the same nucleotide sequence, albeit not methylated, as that of the sample DNA (hereinafter, this PCR amplification product is referred to as a negative control), or a detection signal from the PCR amplification product of bisulfite-treated DNA having the same nucleotide sequence as that of the sample DNA and having a known methylation rate (e.g., 100%) (hereinafter, this PCR amplification product is referred to as a positive control).

Alternatively, the ratio between the abundance of methylated DNA and the abundance of unmethylated DNA in sample DNA can be measured by comparing a detection signal from the PCR amplification product of the bisulfite-treated sample DNA with detection signals from the negative and positive controls. Alternatively, the methylation rate of methylated DNA, its abundance, and the ratio between the abundance of methylated DNA and the abundance of unmethylated DNA in sample DNA can be measured by comparing detection signals from a plurality of PCR amplification products derived from a plurality of bisulfite-treated DNAs each having the same nucleotide sequence as that of the sample DNA and having a known methylation rate (hereinafter, these PCR amplification products are referred to as standards) with a detection signal from the PCR amplification product of the bisulfite-treated sample DNA In the method of the present invention, DNA synthesized chemically or in a genetic engineering manner which consists of the same nucleotide sequence as that of the negative control, the positive control, or the standards may be used instead of the negative control, the positive control, or the standards. In the method of the present invention, a commercially available product can also be used in the preparation of the negative control, the positive control, or the standards, and, for example, EpiTect Control DNA and Control DNA Set (manufactured by Qiagen N.V.) can be used.

In a preferred aspect, for the ion exchange chromatography according to the present invention, a sample containing the PCR amplification product of the bisulfite-treated sample DNA and a sample of the negative control, the positive control, or the standards are individually subjected to ion exchange chromatography analysis. The samples adsorbed on the column can be applied to gradient elution using a plurality of eluents to elute the PCR amplification product of the bisulfite-treated sample DNA and the negative control, the positive control, or the standards at different retention times according to their DNA methylation rates.

The detection signal from the negative control can be acquired by performing bisulfite treatment and PCR according to the procedures mentioned above using DNA having the same nucleotide sequence, albeit not methylated, as that of the sample DNA instead of the sample DNA and subjecting the obtained PCR amplification product to ion exchange chromatography. The detection signal from the positive control can be acquired by performing bisulfite treatment and PCR according to the procedures mentioned above using DNA having the same nucleotide sequence as that of the sample DNA and having a known methylation rate (e.g., 100%) instead of the sample DNA and subjecting the obtained PCR amplification product to ion exchange chromatography. Alternatively, the detection signal from the negative or positive control may be obtained by subjecting the synthesized DNA or the commercially available DNA mentioned above as the negative or positive control to ion exchange chromatography.

The detection signals from the standards can be acquired by performing bisulfite treatment and PCR according to the procedures mentioned above using a plurality of DNAs each having the same nucleotide sequence as that of the sample DNA and having a known methylation rate instead of the sample DNA and subjecting each of a plurality of the obtained PCR amplification products to ion exchange chromatography. Furthermore, a calibration curve may be prepared from the respective detection signals thus obtained. Alternatively, the detection signals from the standards may be obtained by subjecting the synthesized DNA or the commercially available DNA mentioned above as the standards to ion exchange chromatography.

Subsequently, the detection signal obtained by the chromatography from the PCR amplification product of the bisulfite-treated sample DNA is compared with the detection signal from the negative or positive control or the standards. The methylation of the sample DNA can be detected on the basis of the difference in detection signal therebetween.

For example, the sample DNA can be determined as methylated when the peak retention time of the detection signal obtained from the PCR amplification product of the bisulfite-treated sample DNA deviates from the peak retention time of the negative control. In this respect, as the deviation of the retention time is larger, the methylation rate can be presumed to be larger. On the other hand, as the peak retention time of the detection signal obtained from the PCR amplification product of the bisulfite-treated sample DNA deviates more largely from the peak retention time of the 100% methylated positive control, the methylation rate of the sample DNA can be presumed to be smaller. Alternatively, a calibration curve is prepared on the basis of a plurality of peak retention times obtained from the standards having a known methylation rate, and the methylation rate of the sample DNA can be determined on the basis of this calibration curve (see FIGS. 1 and 2).

The calibration curve can establish an association between DNA methylation rates and retention times. Thus, a DNA methylation rate corresponding to the reference retention time (hereinafter, also referred to as a reference DNA methylation rate) can be determined on the basis of the calibration curve. Provided that the reference DNA methylation rate is obtained in advance, a new reference retention time can be easily calculated, even if HPLC equipment or analysis conditions are changed, by applying the reference DNA methylation rate to a calibration curve newly prepared using the changed equipment or conditions.

Also, the abundance ratio of methylated DNA (e.g., the abundance ratio of unmethylated DNA or the abundance ratio of DNA methylated at a particular rate) in sample DNA can be determined, for example, by comparing the peak height or the peak area of the detection signal obtained from the PCR amplification product of the bisulfite-treated sample DNA with the peak height or the peak area of a detection signal obtained from the PCR amplification product of bisulfite-treated DNA having a known methylation rate and mixing ratio of methylated DNA.

In the method of the present invention, examples of the method for determining the presence or absence of the peak of the detection signal obtained by the chromatography include peak detection using existing data processing software, for example, LCsolution (Shimadzu Corp.), GRAMS/AI (Thermo Fisher Scientific, Inc.), or Igor Pro (WaveMetrics). The method for determining the presence or absence of the peak using LCsolution will be described as an example. Specifically, a retention time zone in which a peak is to be detected is first designated. Next, various parameters are set in order to remove unnecessary peaks such as noise. Examples of such settings include setting of the parameter "WIDTH" to larger than the half widths of unnecessary peaks, setting of the parameter "SLOPE" to larger than the leading slopes of unnecessary peaks, and changing of the parameter "DRIFT" setting to select either vertical partitioning or baseline partitioning of peaks with a low degree of separation. The values of these parameters can be set to appropriate values according to a chromatogram because the obtained chromatogram differs depending on analysis conditions, the type of a selected gene marker, the amount of a specimen, etc.

The retention time, i.e., peak top time, can be automatically calculated using the data processing software. For example, first derivation of the chromatogram is carried out, and the time at which the derivative changes from positive to negative can be obtained as the peak top time.

In the method of the present invention, the retention time of the detection signal obtained by the chromatography is examined. As a result, the sample is determined as a sample obtained from a renal cell carcinoma patient with poor prognosis when the detection signal is obtained at a retention time shorter than the reference retention time. As shown in FIGS. 3A and 3B, the peak of DNA having a high methylation rate and the peak of DNA having a low methylation rate are easily separable. In the case of bimodal peaks, the influence of unmethylated DNA can be removed by the separation between the peaks, and the sample obtained from a renal cell carcinoma patient with poor prognosis can be determined accurately.

In the method of the present invention, difference data can be determined by subtracting the detection signal obtained from the negative control from the detection signal obtained from the PCR amplification product of the bisulfite-treated sample DNA. By determining the difference data, a signal from unmethylated DNA (noise) can be removed from detection signals as the whole sample DNA to extract only a signal from methylated DNA. The difference data corresponds to a detection signal derived from methylated DNA in the sample DNA. The retention time of this difference data is compared with the reference retention time. The sample is determined as a sample obtained from a renal cell carcinoma patient with poor prognosis when the result is shorter than the reference retention time. Use of the difference data permits detection or analysis of methylated DNA even in a sample in which a signal component from the methylated DNA is detected only at a weak level, for example, sample DNA having a low abundance ratio of the methylated DNA or sample DNA containing methylated DNA having a low methylation rate. When the sample DNA contains DNAs having various methylation rates, various chromatogram patterns having, for example, a shoulder peak or overlapping peaks, are obtained. In such a case, the prognosis of cancer can be determined highly accurately by determining the difference data, because only a signal of DNA having a high methylation rate in the sample DNA can be extracted.

Thus, use of the difference data permits more highly accurate analysis on methylated DNA in sample DNA. For determining the difference data, it is desirable to use equal DNA levels of the sample DNA and the DNA used as the negative control. The DNA levels can be confirmed by a measurement method such as absorbance measurement.

The procedures of the method for determining the prognosis of cancer according to the present invention using the difference data are basically the same as those for obtaining the data before the subtraction as mentioned above. For example, the retention time of the detection signal obtained by the chromatography is examined, and as a result, the sample is determined as a sample obtained from a renal cell carcinoma patient with poor prognosis when the detection signal is obtained at a retention time shorter than the retention time serving as a reference.

In the method for determining the prognosis according to the present invention, use of the difference data is very effective. A specimen which is collected for clinical examination may contain normal cells such as noncancerous epithelial cells or stromal cells in which DNA methylation has not yet proceeded, or may be rich in cells in a precancerous state in which DNA methylation has not much proceeded. Alternatively, such a specimen may have various ratios of cancer cells having various DNA methylation rates. Use of the difference data can remove the influence of normal cells in the specimen, normal DNA in precancerous cells, or unmethylated DNA derived from cancer cells in which a gene region to be assayed is not methylated. Therefore, the methylated DNA can be detected more highly accurately. Furthermore, the prognosis of cancer can be determined more highly accurately by use of the detection result.

According to the method for determining the prognosis according to the present invention, methylated DNA in a sample can be separated from unmethylated DNA and detected. Therefore, even if the sample is rich in normal cells, the presence of methylated DNA and the methylation rate thereof can be detected highly accurately to precisely determine the prognosis. The method of the present invention permits precise determination of prognosis even for a subject which has not been determined as CIMP-positive by conventional examination in spite of poor prognosis.

EXAMPLES

Hereinafter, the present invention will be described in detail with reference to Examples. However, the present invention is not intended to be limited by Examples given below.

[Patient and Tissue Sample]

109 cancer tissue (T) samples and corresponding 107 noncancerous renal cortical tissue (N) samples were obtained from samples operatively excised from 110 patients affected by primary clear cell renal cell carcinoma. No remarkable histological change was observed in the N samples. These patients did not receive preoperative treatment. These patients had undergone nephrectomy at the National Cancer Center. The patients consisted of 79 males and 31 females with an average age of 62.8±10.3 years old (mean±standard deviation, 36 to 85 years old).

The histological diagnosis of the samples was conducted according to the classification of WHO (see Eble, J. N. et al., "Renal cell carcinoma, WHO Classification of Tumours. Pathology and Genetics of Tumours of the Urinary System and Male Genital Organs", 2004, IARC Press, Lyon, p. 10-43, FIG. 1).

The histological grades of all tumors were evaluated according to the criterion described in "Fuhrman, S. A. et al., Am. J. Surg. Pathol., 1982, Vol. 6, p. 655-663". TNM classification followed "Sobin, L. H. et al., UICC, TNM Classification of Malignant Tumours, 6th edition, 2002, Wiley-Liss, New York, p. 193-195".

The criteria established for hepatocellular cancer (HCC) were adopted as criteria for the macroscopic classification of renal cell carcinoma (see Non Patent Literatures 4 to 6). Type 3 (contiguous multinodular type) HCC has a lower histological degree of differentiation and a higher occurrence rate of intrahepatic metastasis than those of HCC of type 1 (single nodular type) and type 2 (single nodular type with extranodular growth) (see Kanai, T. et al., Cancer, 1987, Vol. 60, p. 810-819).

The presence or absence of blood vessel invasion was examined by microscopically observing slides provided with hematoxylin-eosin staining and Elastica van Gieson staining. The presence or absence of tumor thrombus in the main trunk of the renal vein was examined by macroscopic observation.

This study was conducted after obtainment of written informed consent from all of the patients to be studied here. Also, this study was carried out under the approval of the Ethical Committee of the National Cancer Center.

Reference Example 1

Determination of CIMP Negativity or Positivity by Conventional Method

The determination of CIMP negativity or positivity by a conventional method was conducted according to the MassARRAY method described in Patent Literature 4 (Example 5). The DNA methylation levels at the CpG sites of 17 genes (FAM150A, GRM6, ZNF540, ZFP42, ZNF154, RIMS4, PCDHAC1, KHDRBS2, ASCL2, KCNQ1, PRAC, WNT3A, TRH, FAM78A, ZNF671, SLC13A5, and NKX6-2) (Tables 1 to 4) were detected by the MassARRAY method, which is one of the methods for detecting methylated DNA.

The MassARRAY method is a method which involves amplifying DNA after bisulfite treatment, transcribing the amplification product to RNA, further cleaving the RNA with RNase in a base-specific manner, and then detecting the difference in molecular weight between a methylated DNA fragment and an unmethylated DNA fragment using a mass spectrometer.

First, MassARRAY primers were designed for CpG islands containing the CpG sites using EpiDesigner (primer design software for MassARRAY manufactured by Sequenom).

In order to eliminate the influence of bias in PCR, 3 DNA polymerases and conditions involving approximately 4 annealing temperatures on average per primer set were combined for PCR runs to determine the optimum PCR conditions with good quantitative performance. Furthermore, all of the analyte CpG sites contained in PCR target sequences were confirmed to exhibit good quantitative performance under the adopted PCR conditions. The MassARRAY analysis was carried out on 102 renal cell carcinoma specimens among the 109 renal cell carcinoma tissue samples.

First, fresh frozen tissue samples obtained from the patients were each treated with phenol-chloroform and subsequently dialyzed to extract high-molecular-weight DNA (see Sambrook, J. et al., Molecular Cloning: A Laboratory Manual, 3rd edition, Cold Spring Harbor Laboratory Press, NY, p. 6.14-6.15). Then, 500 ng of the DNA was treated with bisulfite using EZ DNA Methylation-Gold™ kit (manufactured by Zymo Research Corp.). The bisulfite-treated genomic DNA was amplified by PCR, followed by in vitro transcription reaction. Subsequently, the obtained RNA was specifically cleaved at uracil sites with RNase to form fragments differing in length according to the presence or absence of methylation in the genomic DNA of each sample. Then, the obtained RNA fragments were subjected to mass spectrometry by MALDI-TOF MAS (MassARRAY Analyzer 4, manufactured by Sequenom) capable of detecting the difference in the mass of one base. The obtained mass spectrometry result was aligned with the reference sequence using analysis software (EpiTYPER, manufactured by Sequenom). The methylation level was calculated from the mass ratio between the RNA fragment derived from methylated DNA and the RNA fragment derived from unmethylated DNA. The sequences of the primers used in this analysis and the sequences of the PCR amplification products obtained using sets of these primers are shown in Tables 5 and 6 and the Sequence Listing.

TABLE 5

| Primer set name | PCR product size | Forward primer | Reverse primer | Target sequence (sequence of PCR product) |
|---|---|---|---|---|
| SLC13A5_MA_10 | 500 | agaagagagGAAGGAT TTGAATTTGGAGATA TAGTTT (SEQ ID NO: 17) | cagtaatacgactcactata gggagaaggctAAAAAA CCCAAAAACCTACA AAAAA (SEQ ID NO: 18) | SEQ ID NO: 1 |

TABLE 5-continued

| Primer set name | PCR product size | Forward primer | Reverse primer | Target sequence (sequence of PCR product) |
|---|---|---|---|---|
| SLC13A5_MA_13 | 463 | aggaagagagTTTTTTTGGGTTTTGAAGGGTT (SEQ ID NO: 19) | cagtaatacgactcactatagggagaaggctTTATATCCCTTCCTCTCTAAAACTCC (SEQ ID NO: 20) | SEQ ID NO: 2 |
| SLC13A5_MA-15 | 384 | aggaagagagTTTTTTTTGTTTTAGGGGTTGT (SEQ ID NO: 21) | cagtaatacgactcactatagggagaaggctCCACCAACATAAATAAAACTCCCC (SEQ ID NO: 22) | SEQ ID NO: 3 |
| FAM150_MA_14 | 455 | aggaagagagGGGAGGATTTAGTAGGGTAATTGT (SEQ ID NO: 23) | cagtaatacgactcactatagggagaaggctTTTTCACCTAAAAAAACACTAAAACC (SEQ ID NO: 24) | SEQ ID NO: 4 |
| GRM6_MA_8 | 188 | aggaagagagGGTTTAGGATAAGTTTGTGATAGATG (SEQ ID NO: 25) | cagtaatacgactcactatagggagaaggctAAAACAAAAAACAAACCCAAAAT (SEQ ID NO: 26) | SEQ ID NO: 5 |
| ZFP42_MA_2 | 196 | aggaagagagGAGTTGATGGGTGGTTGTAGTTT (SEQ ID NO: 27) | cagtaatacgactcactatagggagaaggctCCCATTTAAAAAAAATTCCATAAAACAAA (SEQ ID NO: 28) | SEQ ID NO: 6 |
| ZNF154_MA_5 | 279 | aggaagagagGGTGAATATATTTTAGAGAAGTTAAAATGG (SEQ ID NO: 29) | cagtaatacgactcactatgggagaaggctTCCCTCCACTACCCTAAAACTTAAA (SEQ ID NO: 30) | SEQ ID NO: 7 |
| RIMS4_MA_9 | 402 | aggaagagagGGAGTTTTAGTTTTATGAGGGAAGGA (SEQ ID NO: 31) | cagtaatacgactcactatagggagaaggctAAACCCCAAAATCTCCAAATAC (SEQ ID NO: 32) | SEQ ID NO: 8 |

TABLE 6

| Target gene name | PCR product size | Forward primer | Reverse primer | Target sequence (sequence of PCR product) |
|---|---|---|---|---|
| TRH_MA_8 | 414 | aggaagagagAATAGATTTTTAGAGGTGGTGTAGAAA (SEQ ID NO: 33) | cagtaatacgactcactatagggagaaggctAAAAAACTCCCTTTCCAATACTCC (SEQ ID NO: 34) | SEQ ID NO: 9 |
| ZNF540_MA_17 | 463 | aggaagagagGGGTAGGGTAGAATTAGGTTAAAGAAA (SEQ ID NO: 35) | cagtaatacgactcactatagggagaaggctACTAAAATCAATAACCCCCAAAAAA (SEQ ID NO: 36) | SEQ ID NO: 10 |
| PCDHAC1_MA_5 | 362 | aggaagagagTGGTAGTTTTTGGGATATAAGAGGG (SEQ ID NO: 37) | cagtaatacgactcactatagggagaaggctAAACTACCCAAATCTTAACCTCCAC (SEQ ID NO: 38) | SEQ ID NO: 11 |
| PRAC_MA_2 | 264 | aggaagagagGGTGAAAGTTTGTTGTTTATTTTTTTT (SEQ ID NO: 39) | cagtaatacgactcactatagggagaaggctCAAACTAAAATTCTAATCCCCACCTT (SEQ ID NO: 40) | SEQ ID NO: 12 |

TABLE 6-continued

| Target gene name | PCR product size | Forward primer | Reverse primer | Target sequence (sequence of PCR product) |
|---|---|---|---|---|
| ZNF671_MA_8 | 428 | aggaagagagTGGGATATAGGGGTTGTAGGTATTT (SEQ ID NO: 41) | cagtaatacgactcactatagggagaaggctATAAAAACCACACTCTACCCACAAA (SEQ ID NO 42) | SEQ ID NO: 13 |
| WNT3A_MA_9 | 348 | aggaagagagGTTTATTTGGTAATGAGGGGTTGTT (SEQ ID NO: 43) | cagtaatacgactcactatagggagaaggctTTCCTCAATCTTAAACATCTCAAAA (SEQ ID NO: 44) | SEQ ID NO: 14 |
| KHDRBS2_MA_19 (rev) | 422 | aggaagagagTTTGGTATTATTATTAATGAGTGGTTGG (SEQ ID NO: 45) | cagtaatacgactcactatagggagaaggctAACAAATCCTACCTTCTACCAAAAAA (SEQ ID NO: 46) | SEQ ID NO: 15 |
| ASCL2_MA_8 | 339 | aggaagagagGTTAATAAAGTTGGGTTTTTGTTGG (SEQ ID NO: 47) | cagtaatacgactcactatagggagaaggctAATACAAACCTCCAAACCCTCC (SEQ ID NO: 48) | SEQ ID NO: 16 |

The DNA methylation levels of the CpG sites were detected for all of the MassARRAY analyte regions to differentiate between renal cell carcinoma having poor prognosis (CIMP-positive group: 14 specimens) and renal cell carcinoma having good prognosis (CIMP-negative group: 88 specimens).

Reference Example 2

Preparation of Anion Exchange Column

In a reactor equipped with a stirrer, a mixture of 200 g of tetraethylene glycol dimethacrylate (manufactured by Shin-Nakamura Chemical Co., Ltd.), 100 g of triethylene glycol dimethacrylate (manufactured by Shin-Nakamura Chemical Co., Ltd.), 100 g of glycidyl methacrylate (manufactured by Wako Pure Chemical Industries, Ltd.), and 1.0 g of benzoyl peroxide (manufactured by Kishida Chemical Co., Ltd.) was added to 2,000 mL of an aqueous solution containing 3 wt % of polyvinyl alcohol (manufactured by The Nippon Synthetic Industry Co., Ltd.). The reaction mixture was heated with stirring and polymerized at 80° C. for 1 hour in the nitrogen atmosphere. Next, 100 g of ethyl methacrylate trimethylammonium chloride (manufactured by Wako Pure Chemical Industries, Ltd.) was dissolved as the hydrophilic monomer having the strong cationic group in ion exchange water. This solution was added to the reactor mentioned above. Similarly, the reaction mixture was polymerized with stirring at 80° C. for 2 hours in the nitrogen atmosphere. The obtained polymer composition was washed with water and acetone to obtain coated polymer particles having, on the surface, a hydrophilic polymer layer having a quaternary ammonium group. The obtained coated polymer particles were found to have an average particle size of 10 μm by measurement using a particle size distribution measurement apparatus (AccuSizer 780, manufactured by Particle Sizing Systems).

10 g of the obtained coated polymer particles was dispersed in 100 mL of ion exchange water to prepare pre-reaction slurry. Subsequently, 10 mL of N,N-dimethylaminopropylamine (manufactured by Wako Pure Chemical Industries, Ltd.) was added to this slurry with stirring, and the mixture was reacted at 70° C. for 4 hours. After the completion of the reaction, the supernatant was removed using a centrifuge (manufactured by Hitachi, Ltd., "Himac CR20G"), and the residue was washed with ion exchange water. After the washing, the supernatant was removed using a centrifuge. This washing with ion exchange water was further repeated four times to obtain a packing material for ion exchange chromatography having a quaternary ammonium group and a tertiary amino group on the surface of the substrate particles.

A stainless column (column size: inside diameter 4.6 mm×length 20 mm) of a liquid chromatography system was packed with the packing material for ion exchange chromatography.

Reference Example 3

Detection of Methylated DNA by Ion Exchange Chromatography (1) Extraction and Bisulfite Treatment of Genomic DNA Fresh frozen tissue samples obtained from the patients were each treated with phenol-chloroform and subsequently dialyzed to extract high-molecular-weight DNA (see Sambrook, J. et al., Molecular Cloning: A Laboratory Manual, 3rd edition, Cold Spring Harbor Laboratory Press, NY, p. 6.14-6.15). 500 ng of the DNA was treated with bisulfite using EZ DNA Methylation-Gold™ kit (manufactured by Zymo Research Corp.).

(2) PCR

The bisulfite-treated genomic DNA obtained in the preceding step (1) was amplified by PCR. The PCR was performed using a 25 μL of a reaction solution containing 10 ng of template DNA, GeneAmp 1×PCR buffer (manufactured by Life Technologies Corp.), 200 μmol/L GeneAmp dNTP Mix (manufactured by Life Technologies Corp.), 0.75 U AmpliTaq Gold DNA Polymerase (manufactured by Life Technologies Corp.), and 0.25 μmol/L forward and reverse primers. The PCR involved initial thermal denaturation at 95° C. for 5 minutes, followed by 35 cycles each involving 94° C. for 30 seconds→59° C. (in the case of using F3-R3 primer) for 30 seconds→72° C. for 40 seconds, and subsequent elongation reaction at 72° C. for 10 minutes. After the completion of the PCR, 5 µL of the reaction solution was mixed with 1 µL of a loading dye solution, then applied to a 3% agarose gel supplemented with ethidium bromide in advance, and electrophoresed. The PCR amplification product was observed to confirm that the PCR amplification product of interest was obtained. The sequence of each primer is shown in Table 7.

TABLE 7

| Target gene name | Product size | Target Seq |
|---|---|---|
| FAM150A_ MA_14 0% methylation | 384 | <u>GGGAGGACCCAGTAGGGTAACTGC</u>TGTGTTGCCCTGGTGGTTC TCCCTGGGCTCTGTCTCCTGCTGCCTCCACCCCCTGAGCCTTG GGGTCTGTCATGGCTTCCCCTGGCTGGTGGGGTCAGTAGAACC TGTGGTGCCTAGGTCTGGATGGAAAAAAGCAGGGCTGGGGTGT GGCCTGGATGAGIGGAGATCTCTGTGCCITGGGCTCAAAGGIG TGGGGTGTGCTCTGCTGCTGAGCCCCTGCTTGCTCAGGAACAC TGGCCATGCTGTCATGCCAGCTGCCCCTGCCCCAGGTCTGGAG GCCTGACCTGCTCTCCTAGGTGCAGCACTGTGTTCTCTTCTGT GTGGGGAGTGGTGGGTG<u>GAAGAGGTCTGGGGCTGGGCAC</u> (SEQ ID NO: 49) |
| FAM150A_ MA_14 100% methylation | 384 | <u>GGGAGGACCCAGTAGGGTAACTGC</u>CGCGTCGCCCCGGCGGTTC TCCCTGGGCTCTGTCTCCCGCCGCCTCCACCCCCGAGCCTTG GGGTCCGTCACGGCTTCCCCTGGCTGGCGGGGTCAGTAGAACC CGCGGCGCCTAGGTCCGGACGGAAAAAAGCAGGGCCGGGGTGC GGCCTGGATGAGCGGAGATCTCCGCGCCTTGGGCTCAAAGGTG CGGGGTGCGCTCTGCTGCCGAGCCCCTGCTCGCTCAGGAACAC TGGCCACGCCGTCACGCCAGCCGCCCCTGCCCCAGGTCTGGAG GCCCGACCTGCTCTCCTAGGCGCAGCACCGCGTTCTCTTCCGC GTGGGGAGCGGCGGGC<u>GGAAGAGGTCTGGGGCTGGGCAC</u> (SEQ ID NO: 50) |
| Primer | forward reverse | GGGAGGATTTAGTAGGGTAATTGT (SEQ ID NO: 51) ATACCCAACCCCAAACCTCTTC (SEQ ID NO: 52) |

Primer binding sites are underlined.

(3) HPLC Analysis

The anion exchange column prepared in Reference Example 2 was used in ion exchange chromatography under the following conditions to separate and detect each PCR amplification product obtained in the preceding step (2).

System: LC-20A series (manufactured by Shimadzu Corp.)

Eluent: eluent A: 25 mmol/L tris-HCl buffer solution (pH 7.5)
eluent B: 25 mmol/L tris-HCl buffer solution (pH 7.5)+1 mol/L ammonium sulfate Analysis time: 15 min Elution method: the mixing ratio of eluent B was linearly increased under the following gradient conditions:

0 min (40% eluent B)→10 min (100% eluent B) Specimen: the PCR amplification product obtained in the step (2)

Flow rate: 1.0 mL/min
Detection wavelength: 260 nm
Sample injection volume: 5 µL
Column temperature: 70° C.

Example 1

Variation in Chromatography Retention Time Caused by DNA Methylation Rate

On the basis of the DNA sequence of a 384-bp region having 39 CpG sites in a FAM150A gene promoter, 8 DNAs differing in methylation rate were synthesized from DNA in which all of the 39 CpG sites were methylated (100% methylated DNA) through DNA in which none of the 39 CpG sites were methylated (0% methylated DNA). The 50% methylated DNA was synthesized as 3 patterns of DNA having a methylation position closer to the 5' end, closer to the 3' end, and closer to the center, respectively. The methylation rate of each synthesized DNA and the number of its methylated sites in the CpG island are shown in Table 8.

TABLE 8

| Synthesized DNA No. | Methylation rate (position on CpG island) | The number of methylated CpG sites | The number of unmethylated CpG sites |
|---|---|---|---|
| 1 | 100% | 39 | 0 |
| 2 | 0% | 0 | 39 |
| 3 | 25% (random) | 10 | 29 |
| 4 | 50% (random) | 20 | 19 |
| 5 | 75% (random) | 30 | 9 |
| 6 | 50% (closer to 5' end) | 20 | 19 |
| 7 | 50% (closer to 3' end) | 20 | 19 |
| 8 | 50% (center) | 20 | 19 |

Figure 2:
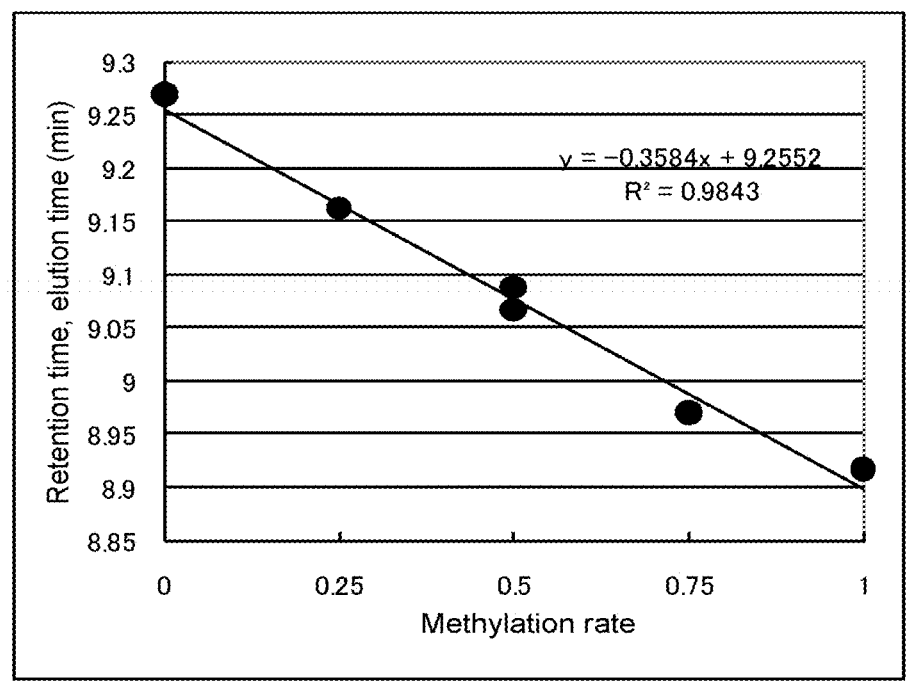
FIG. 2 shows the correlation between DNA methylation rates and chromatography retention times.

The 8 synthesized DNAs were subjected to PCR, and HPLC according to the procedures of Reference Example 3. The HPLC chromatograms of synthesized DNA No. 1 (100% methylation), No. 2 (0% methylation), No. 3 (25% methylation), No. 4 (50% methylation), and No. 5 (75% methylation) are shown in FIG. 1. Reduction in retention time according to the DNA methylation rate was found. Data obtained by plotting the methylation rates of the 8 DNAs vs. HPLC retention times is shown in FIG. 2. The HPLC retention times exhibited very high correlation with the DNA methylation rates. The 50% methylated DNAs were confirmed to exhibit almost the same retention time, irrespective of their methylation positions. This demonstrated that retention times are determined depending on methylation rates, irrespective of methylation positions in DNA.

Thus, the methylation rate of CpG sites contained in sample DNA can be measured by measuring the HPLC retention time.

Example 2

DNA Methylation Analysis and Prognosis Determination for Renal Cell Carcinoma

Genomic DNA was prepared from each of CIMP-positive renal cell carcinoma in 13 patients and CIMP-negative renal cell carcinoma in 5 patients determined as having CIMP-positive or -negative renal cell carcinoma in Reference Example 1. The DNA was subjected to bisulfite treatment, PCR, and HPLC according to the procedures of Reference Examples 3(1) to 3(3). In PCR, a 384-bp region in a FAM150A gene promoter was amplified.

Furthermore, each DNA having a methylation rate of 0% (negative control) or 100% (positive control) in the PCR amplification region was also analyzed by HPLC according to the same procedures as above.

Figure 3:
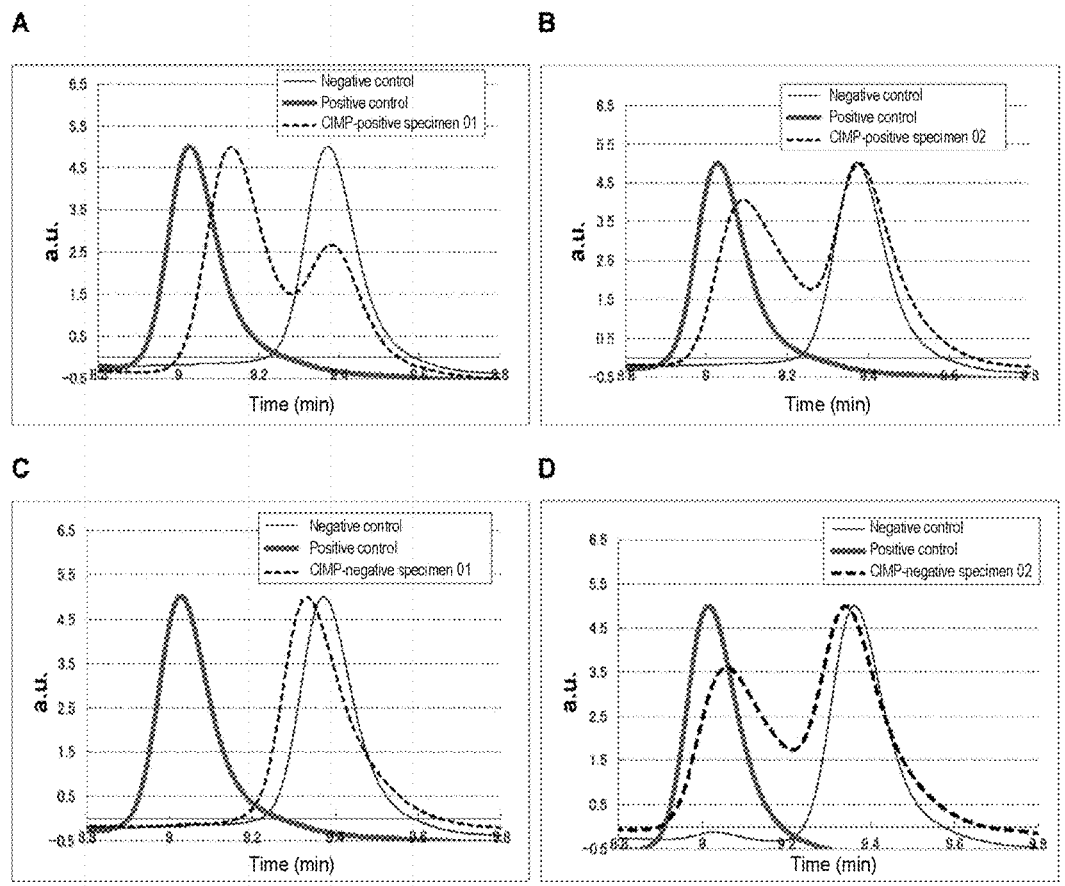
FIG. 3 shows chromatograms of CIMP-positive and -negative samples.

The HPLC chromatograms obtained from the CIMP-positive and CIMP-negative samples are shown in FIG. 3.

FIG. 3 also shows the chromatograms of the unmethylated DNA (negative control) and the 100% methylated DNA (positive control). FIGS. 3A and 3B are the chromatograms of the CIMP-positive samples, and a peak differing in retention time from the peak of the unmethylated DNA (negative control) appeared clearly, indicating the presence of methylated DNA. FIG. 3C is the chromatogram of the CIMP-negative sample, and its peak was hardly able to be discriminated from the peak of the unmethylated DNA (negative control) at their retention times, indicating that methylated DNA was almost absent. FIG. 3D is the chromatogram of the CIMP-negative sample, though a peak differing in retention time from the peak of the unmethylated DNA (negative control) appeared clearly, indicating the presence of methylated DNA. This suggests the possibility that this sample was a specimen with poor prognosis even though determined as CIMP-negative.

Figure 4:
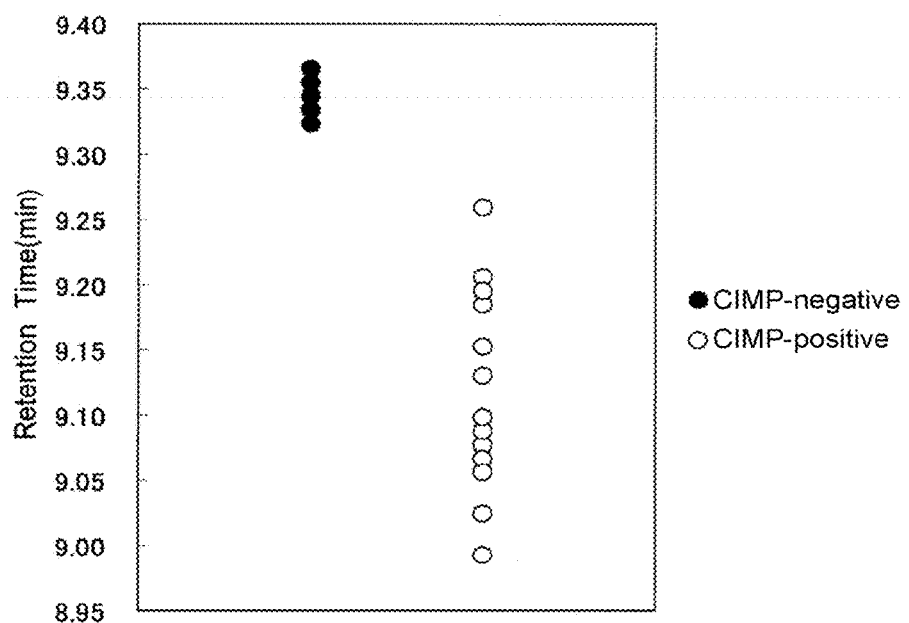
FIG. 4 shows chromatography retention times of CIMP-positive and -negative samples.

FIG. 4 is a diagram in which the peak retention times of HPLC chromatograms were plotted for all of the 18 CIMP-negative or -positive samples examined in this Example. The CIMP-negative samples and -positive samples differed evidently in retention time distribution, demonstrating that CIMP of cancer determined by the MassARRAY method can also be precisely analyzed by the method of the present invention.

For the 384-bp region of the FAM150A gene promoter used in this Example, the retention time serving as a reference can be set to a retention time of approximately 9.3 min because, as shown in FIG. 4, the retention time of approximately 9.3 min differentiates between the CIMP-positive group and the CIMP-negative group. Specifically, a specimen having a detection signal at a retention time shorter than the retention time serving as a reference (reference retention time) can be determined as having poor prognosis. The reference retention time mentioned above can be set to a reference retention time appropriate for HPLC analysis conditions, a region of genomic DNA, or the type of a gene marker, etc., because a chromatogram varies depending on these conditions, etc. It is also preferred to set the reference retention time in consideration of necessary clinical sensitivity.

In this Example, the positive control (DNA methylation rate: 100%) exhibited a retention time of approximately 9.0 minutes, and the negative control (DNA methylation rate: 0%) exhibited a retention time of approximately 9.35 minutes. Therefore, the reference DNA methylation rate bringing about the reference retention time was calculated as approximately 17%. Thus, a specimen having a DNA methylation rate higher than the reference DNA methylation rate (approximately 17°) in the 384-bp region of the FAM150A gene promoter used in this Example was found to have poor prognosis.

Figures 1, 5:
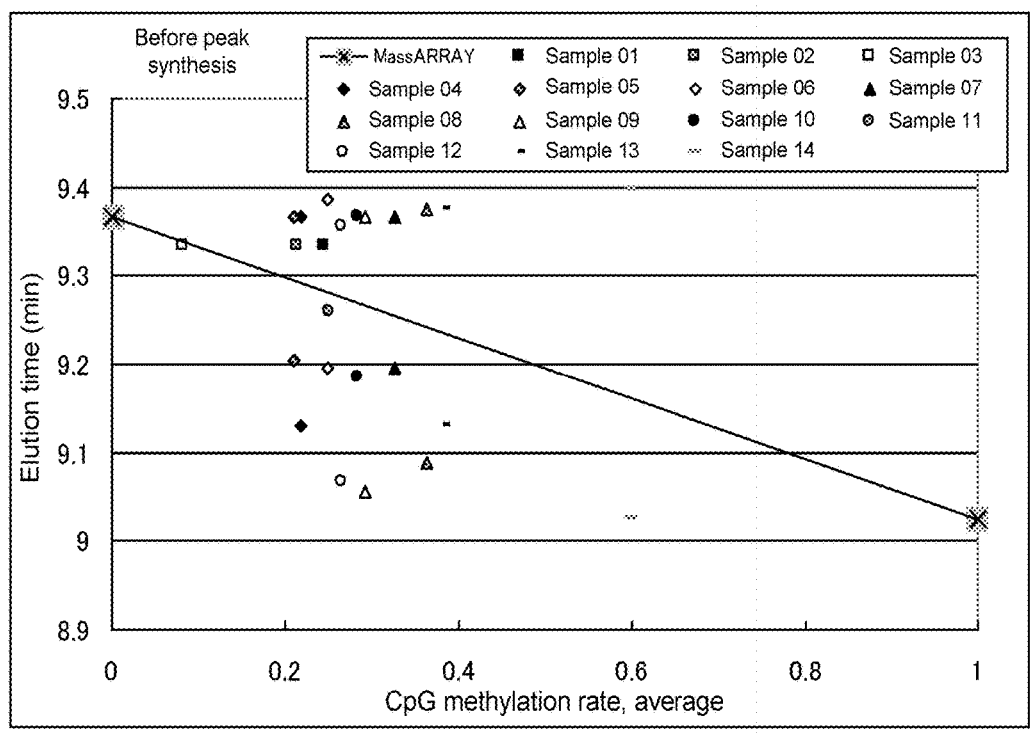
Figures 2, 5:
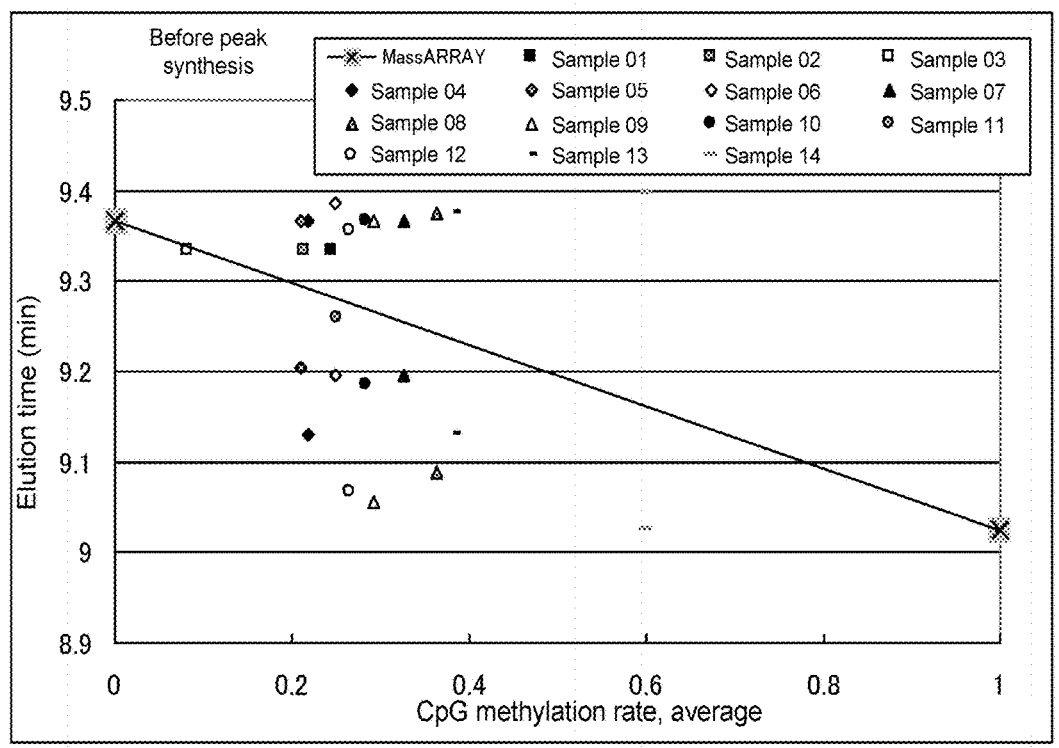

The average DNA methylation level obtained in MassARRAY is compared with the DNA methylation rate obtained in the method of the present invention. As for the bimodal peaks as shown in FIGS. 3A and 3B of the detection signal obtained in the method of the present invention, DNA methylation rates calculated from the retention time (the retention time at which elution occurred faster was defined as a, and the retention time at which elution occurred later was defined as b) were plotted and compared with the DNA methylation rate obtained in MassARRAY. The results are shown in FIG. 5-1. In FIG. 5-1, the DNA methylation rates obtained by these methods do not seem to correlate with each other. On the other hand, a DNA methylation rate obtained from synthetic peak C (retention time c) calculated from the average of the retention time a and the retention time b was plotted and similarly compared with the DNA methylation rate obtained in MassARRAY. The results are shown in FIG. 5-2. As shown in FIG. 5-2, the DNA methylation rate calculated from synthetic peak C correlates favorably with the average DNA methylation rate obtained in the MassARRAY method.

According to the present invention, for example, a sample having 30% methylated DNA and 70% methylated DNA mixed in equal amounts and a sample having only 50% methylated DNA can be clearly distinguished therebetween on the chromatograms. In contrast to this, the MassARRAY method in this example merely produces information showing 50% methylated DNA as an average value from both of the samples. According to the present invention, unlike the MassARRAY method, signals with various DNA methylation rates in a sample can be separated and detected. Therefore, non-averaged DNA methylation rates can be obtained.

The value of a DNA methylation rate obtained by a method such as MassARRAY method or pyrosequencing is obtained as an average DNA methylation rate of the whole sample subjected to the assay. Therefore, a problem of such a method is that the method consequently fails to determine the presence or absence of cells having highly methylated DNA. According to the present invention, the influence of unmethylated DNA can be removed to detect whether or not even a sample determined as CIMP-negative contains highly methylated DNA. Therefore, a risk of estimating DNA methylation rates to be lower than actual values is avoided. Furthermore, a specimen suspected of poor prognosis can be determined.

The determination of CIMP by the method described in Patent Literature 4 involves examining methylation at CpG sites in the target CpG islands of a plurality of gene markers to determine CIMP positivity or CIMP negativity. According to the present invention, the possibility has been suggested that the prognosis of renal cell carcinoma can be easily determined even from a single gene marker at the same level as the CIMP determination by examining the detection signal obtained by HPLC. Furthermore, the possibility has been suggested that the prognosis can be determined more highly accurately by analyzing detection signals from a plurality of gene markers by HPLC.

The invention claimed is:

1. A method for determining a tissue having renal cell carcinoma, comprising:
   (1) treating genomic DNA prepared from a renal tissue of a subject with bisulfite;
   (2) amplifying the bisulfite-treated genomic DNA by PCR, with PCR primers having the nucleotide sequences of SEQ ID NOs: 51 and 52;
   (3) subjecting the PCR amplification product obtained in (2) to ion exchange chromatography;
   (4) obtaining a retention time of a detection signal obtained by the chromatography; and
   (5) determining the tissue as a tissue having renal cell carcinoma obtained from a renal cell carcinoma patient with poor prognosis when the retention time of the detection signal obtained by the chromatography is shorter than a retention time serving as a reference.

2. The method of claim 1, wherein the bisulfate-treated genomic DNA to be amplified by PCR comprises a FAM150A gene promoter region.

3. The method of claim 1, further comprising, before the obtaining of the retention time:
   (1') treating unmethylated DNA corresponding to a region in the genomic DNA to be amplified by the PCR with bisulfite;
   (2') amplifying the bisulfite-treated unmethylated DNA by PCR, with PCR primers having the nucleotide sequences of SEQ ID NOs: 51 and 52;
   (3') subjecting the PCR amplification product obtained in (2') to ion exchange chromatography; and
   (3a) obtaining difference data by subtracting a detection signal obtained by the chromatography in (3') from a detection signal obtained by the chromatography in (3).

4. A method for determining the prognosis of a renal cell carcinoma patient, comprising:
   (1) treating genomic DNA prepared from a renal tissue of a subject with bisulfite;
   (2) amplifying the bisulfite-treated genomic DNA by PCR, with PCR primers having the nucleotide sequences of SEQ ID NOs: 51 and 52;
   (3) subjecting the PCR amplification product to ion exchange chromatography;
   (4) obtaining a retention time of a detection signal obtained by the chromatography; and
   (5) determining the renal cell carcinoma of the subject as having poor prognosis when the retention time of the detection signal obtained by the chromatography is shorter than a retention time serving as a reference.

5. The method of claim 4, wherein the bisulfite-treated genomic DNA to be amplified by PCR comprises a FAM150A gene promoter region.

6. The method of claim 4, further comprising, before the obtaining of the retention time:
   (1') treating unmethylated DNA corresponding to a region in the genomic DNA to be amplified by the PCR with bisulfite;
   (2') amplifying the bisulfite-treated unmethylated DNA by PCR, with PCR primers having the nucleotide sequences of SEQ ID NOs: 51 and 52;
   (3') subjecting the PCR amplification product obtained in (2') to ion exchange chromatography; and
   (3a) obtaining difference data by subtracting a detection signal obtained by the chromatography in (3') from a detection signal obtained by the chromatography in (3).

7. A method for obtaining data for determining a tissue having renal cell carcinoma, comprising:

(1) treating genomic DNA prepared from a renal tissue of a subject with bisulfite;
(2) amplifying the bisulfite-treated genomic DNA by PCR, with PCR primers having the nucleotide sequences of SEQ ID NOs: 51 and 52;
(3) subjecting the PCR amplification product to ion exchange chromatography;
(4) obtaining a retention time of a detection signal obtained by the chromatography; and
(5) determining whether or not the retention time obtained in (4) is shorter than a retention time serving as a reference and determining whether or not the tissue is a tissue having renal cell carcinoma obtained from a renal cell carcinoma patient with poor prognosis.

8. The method of claim 7, wherein the bisulfite-treated genomic DNA to be amplified by PCR comprises a FAM150A gene promoter region.

9. The method of claim 7, further comprising, before the obtaining of the retention time:
(1') treating unmethylated DNA corresponding to a region in the genomic DNA to be amplified by the PCR with bisulfate;
(2') amplifying the bisulfite-treated unmethylated DNA by PCR, with PCR primers having the nucleotide sequences of SEQ ID NOs: 51 and 52;
(3') subjecting the PCR amplification product obtained in (2') to ion exchange chromatography; and
(3a) obtaining difference data by subtracting a detection signal obtained by the chromatography in (3) from a detection signal obtained by the chromatography in (3).

* * * * *

SEQUENCE LISTING

<160> NUMBER OF SEQ ID NOS: 52

<210> SEQ ID NO 1
<211> LENGTH: 500
<212> TYPE: DNA
<213> ORGANISM: Homo sapiens

<400> SEQUENCE: 1

| | | | | | | |
|---|---|---|---|---|---|---|
| gaaggacttg | aacttggaga | catagctcag | cgccgaggcc | atcgcgcggg | agggagactg | 60 |
| gcgggcgaga | cgagtgaggg | gcagctagag | gcgccgcggg | cttaagaagg | ggccacagtc | 120 |
| cccgggggatt | ggggagggggg | cggtgacaac | tccgccccgc | acggggggcgc | ctccccgcgg | 180 |
| ccctggggcg | gggccacccc | tcggggtctg | tgggacgcgc | ctgcccccaa | ttctgccacc | 240 |
| cggcggcggt | gggaggcgtc | tttggactcc | aacgcttcgg | gccagccctc | taggggcagc | 300 |
| ctgggcccta | gcatctcgcg | ctgtccaagc | ctctcctgcg | ctgccgaggc | agaggtgcgt | 360 |
| cccgggggctg | ccaagcgggg | cgtgttttgg | tcactggtgc | tgcccgcttt | ggcgtaaggc | 420 |
| gccctcccgc | gtccgcatct | gctctttcct | gggctctgaa | gggtcccgga | tgaaactctc | 480 |
| tgcaggcctc | tgggtctctc | | | | | 500 |

<210> SEQ ID NO 2
<211> LENGTH: 463
<212> TYPE: DNA
<213> ORGANISM: Homo sapiens

<400> SEQUENCE: 2

| | | | | | | |
|---|---|---|---|---|---|---|
| ctttcctggg | ctctgaaggg | tcccggatga | aactctctgc | aggcctctgg | gtctctcagg | 60 |
| tctatctccc | cgatctccct | ctcctttcca | tctccttact | tccgcccctc | cggtgtctct | 120 |
| ccgagaggtg | tccccccacg | ccccgcgccc | tccgcaccgc | gggcctcgct | tcccggtccc | 180 |
| ccctggcttc | ctcgccacgt | ccgccccact | ctaggtgcag | gaccccttt | ccccgctcgc | 240 |
| actctccggc | ccggagctcc | tgggcgatcg | cacaggggaag | cgaggccact | gtcctcctct | 300 |
| gtcccagggg | ctgtcgcgct | ccagtggacg | ctgcaccccg | cagacgcccg | gcgggcagat | 360 |
| gcggacacgc | gtcttggagg | ggccccaccg | agcctcagca | gccgcagctg | cccgcccgac | 420 |
| ccaggtcaga | gggaaacgga | gctctagaga | ggaagggaca | caa | | 463 |

<210> SEQ ID NO 3
<211> LENGTH: 384
<212> TYPE: DNA
<213> ORGANISM: Homo sapiens

<400> SEQUENCE: 3

| | | | | | | |
|---|---|---|---|---|---|---|
| cctcctctgt | cccagggggct | gtcgcgctcc | agtggacgct | gcaccccgca | gacgcccggc | 60 |
| gggcagatgc | ggacacgcgt | cttggagggg | ccccaccgag | cctcagcagc | cgcagctgcc | 120 |
| cgcccgaccc | aggtcagagg | gaaacggagc | tctagagagg | aagggacaca | actaaggcga | 180 |
| cactgagaca | gtcgcccatg | tattcattca | gcccgccagg | caacagacag | gtgccgagca | 240 |
| cctcttctcc | gcgaggccct | gttttgggca | ctggagacac | acggatgcaa | agacatcccc | 300 |
| acctctgtga | ttttcttctt | tcctctcctc | tgcctgcctc | tcattctgca | gcttcctttt | 360 |
| ggggagtctc | atccatgctg | gtgg | | | | 384 |

<210> SEQ ID NO 4
<211> LENGTH: 455
<212> TYPE: DNA
<213> ORGANISM: Homo sapiens

<400> SEQUENCE: 4

```
gggaggaccc agtagggtaa ctgccgcgtc gccccggcgg ttctccctgg gctctgtctc      60
ccgccgcctc caccccccga gcctcggggt ccgtcacggc ttcccctggc tggcggggtc     120
agtagaaccc gcggcgccta ggtccggacg gaaaaaagca gggccgggt gcggcctgga      180 tgagcggaga tctccgcgcc ttgggctcaa aggtgcgggg tgcgctctgc tgccgagccc     240
ctgctcgctc aggaacactg gccacgccgt cacgccagcc gccctgccc caggtctgga      300 ggcccgacct gctctcctag gcgcagcacc gcgttctctt ccgcgtgggg gagcggcggg     360
cggaagaggt ctggggctgg gcaccgggga cacgcgccca gctcccctgg cctccctggg     420
gggagtggcc ggtttcagtg cttccccagg tgaaa                                455
```

<210> SEQ ID NO 5
<211> LENGTH: 188
<212> TYPE: DNA
<213> ORGANISM: Homo sapiens

<400> SEQUENCE: 5

```
ggttcaggac aagtctgtga cagatgcggc cgaggccctg agcgagagag gatttaagga      60
ttctagggag ggatgagaga ccgctccgag ggtggagacc cctcctgagt gtgggggtg      120 gcggtgctgg ctctccccgc atctccttcc cctccctctc ccaatctctg gtctgttt      180 cctgtttt                                                              188
```

<210> SEQ ID NO 6
<211> LENGTH: 196
<212> TYPE: DNA
<213> ORGANISM: Homo sapiens

<400> SEQUENCE: 6

```
gagctgatgg gtggctgtag cctgattaga ccgcgtcagt ccggagggtg ggtcttggga      60
gggggcgcag ggcagtccac gttccactg cagtttctcc tttgttttac gtttgggagg     120
aggtggcatt ggaaatagca gagtgcttcg cggtaacagg ggtgagtctt gtttcatgga    180
acttttttca aatggg                                                     196
```

<210> SEQ ID NO 7
<211> LENGTH: 279
<212> TYPE: DNA
<213> ORGANISM: Homo sapiens

<400> SEQUENCE: 7

```
ggtgaacaca cctcagagaa gctaaaatgg ccgccacgaa gaggcccccc caaaagtccc      60
gtcctttctt tttgtgactc tcaaggaaag tcggttttct gagctcttac tggcttagta    120
gcgtggcgtt caacgcagag cattctaggt aatgtagttt tcatagatcc cgaggtgggt    180 gccgggacc ctttgcacca acctcttgga gtaaaagcga agctccaggg cgctgggcga     240
tgagaaatgg cttatccaag tcctagggca gtggaggga                            279
```

<210> SEQ ID NO 8
<211> LENGTH: 402
<212> TYPE: DNA
<213> ORGANISM: Homo sapiens

<400> SEQUENCE: 8

```
ggagccccag cccatgaggg aaggagagga gagataaatg ggggcgctca aggcctgggg      60
```

```
cgccgggcag gggtcttggg cagggatcct ctggatgtgg ccaagacaaa gatggagagg        120
taaggtctgc gcgccacctc caatggcggg gggcgcgtcg gagccccagg ggtgggacgg        180
ccaaagccca gggcttgaag agtgggcaca ttcaggagac tcagggaggg tggcaggtcg        240
gctccaggga cgaggcaagg ggcctccaat aggcgcgggt gaggagggag atgggtcctg        300
gcgacccaaa gggcccacct gcgggaaagg tgaatgcaga caatctcggg gtccctgggg        360
gagaaggcca aaggtagcg catcctggag accctggggt cc                           402

<210> SEQ ID NO 9
<211> LENGTH: 414
<212> TYPE: DNA
<213> ORGANISM: Homo sapiens

<400> SEQUENCE: 9
aacagatctc cagaggtggt gcagaaacga ccccgcgccg gcgccccatc ctgcggccag         60
tgcctccgcg ccccggctcc ggtccccacc gtccccgccc cagatttccg gaggagcagg        120
cgggcggggt cccgcggggc cggctgccgt cagcgccccc tccccggcgg cgcgaccccct      180 ccccgctgac ctcactcgag ccgccgcctg gcgcagatat aagcggcggc ccatctgaag        240
agggctcggg aggcgcccgg ggtcctcagc gctgcagact cctgacctgc cgactgcgga        300
tcccgagtcc ccggatcccg gacccatcct gtggagccca ctcctggcag gtaaccgccc        360 caaccccctct ccttccgcag acggtgtccg ggagcactgg aaagggagcc ctct             414

<210> SEQ ID NO 10
<211> LENGTH: 463
<212> TYPE: DNA
<213> ORGANISM: Homo sapiens

<400> SEQUENCE: 10
gggcagggca gaaccaggct aaagaaacgt ccagcgtagc ttcaaggatg caccgcgtga         60
tccctatcgg atctccccga cgcgtcaggc ctgcctagac ggtgctggga gcgcgtctcc        120
ttgaacgttg tcccgcctgg gattgcgagg taggtaccgc ctgcctgtgt gtaccggggc        180
tgctgtctcc ggggagggc ttctggcgga caggagaacc aagcagcctc aggagctgcc         240
tgggtgtgtg tgtttctgtg cgagtgttgc atatctctgt gtgtgtttct gtgcaagtgt        300
tgcatgtctg tgtgtgtggg gggggtgtg tctggtgaaa agaatgtgtc tcgtgcggtg        360
gagcgccgtt tctctgtagt ccgcgggctc tcttatgcgc cctcttgtgg tcccaagtgt       420
gcttttcttg tttttcgctt tcttgggggt cattgatttc agc                          463

<210> SEQ ID NO 11
<211> LENGTH: 362
<212> TYPE: DNA
<213> ORGANISM: Homo sapiens

<400> SEQUENCE: 11
tggcagctcc tgggatacaa gagggtgcag gacagacttc aacccgcagc aggatccagc         60
gcggaaagct ctgcagcagg atccagcgcg gaaagccccc cgcagcactt ctttcgggg         120 gctcctgttt ccttaagcct agaaggtgtg gtcgctcacg ttcaccgtcc cgcctctcgc        180
cgcctccgct cggcagctcc acgctgagtc ccgccctctc cgccggagag gtgcgccggg        240
gtcagagcgc cgggacccga cgcgcggctc ccaaagggcg gcaggaagag cccagctggg        300
ctcagccaca gttatcagca atctgcgggc agaggatgtg gaggttaaga tctgggcagc        360
ct                                                                       362
```

<210> SEQ ID NO 12
<211> LENGTH: 264
<212> TYPE: DNA
<213> ORGANISM: Homo sapiens

<400> SEQUENCE: 12

```
ggtgaaagcc tgctgctcac ccttcccttg tttcccaaaa cttctgaagg ctcccaaatt      60
cctgggagac cctctcccag ggcctcctga tgcagctacc atactgagcg atccgtcgat     120
aacgcccttg gcccaccgat cagtttacct tattagagag aaaagcactc ttggaggtag     180
taagatgggc cggtccttga tctgagaaat gggcgcacaa catcgctgtt ctctctgcaa     240
aggtggggac cagaatccag cttg                                            264
```

<210> SEQ ID NO 13
<211> LENGTH: 428
<212> TYPE: DNA
<213> ORGANISM: Homo sapiens

<400> SEQUENCE: 13

```
tgggacacag gggctgcagg cactttacga ttcggagtcg agaaagggt gactgagggc       60
ccggaggacg cagcacccac ccgcgcggag tccgttagct ccgccatagg accgtgggcg     120
cggacagctg ccgggagcgg caggcgtctc gatcggggac gcaggcactt ccgtccctgc     180
agagcatcag acgcgtctcg ggacactggg acaacatct cctccgcgct ttcccaacac      240
ctccacctgc ggcccacaca agcgttacag aaccccggcc agggacagcc tgacagaaac     300
aaaatgtccg ctacaaggag gagccggaag tcccgcccac gcaccccccg caggcactga     360
aacacccctc tcctgggccc tcattgggta tgcaacgtat aggtttgtgg gtagagtgtg     420
gttcccac                                                              428
```

<210> SEQ ID NO 14
<211> LENGTH: 348
<212> TYPE: DNA
<213> ORGANISM: Homo sapiens

<400> SEQUENCE: 14

```
gtccacctgg caatgagggg ctgctgtaga gagagttaag ggtgagttaa gcacggggtg      60
tgagggctc caggaccctc aatcagaaag cgctgtgctg cgcctccac accagaaaag      120
gcgcgttccg tgagaccctc cccagcctgg cgatggaagt gcagataaac caaaggaagg     180
gtcccgaaag gtctctctca ggcctccac ctccactgca catatcctgt ggggaggggga     240
acggtggcca cactttcgcc agggcttgtg atccctcaga gccctcacca agcaaggatc     300
accccagttc cgaattaagg gcgctctgag atgcccaaga ttgaggaa                  348
```

<210> SEQ ID NO 15
<211> LENGTH: 422
<212> TYPE: DNA
<213> ORGANISM: Homo sapiens

<400> SEQUENCE: 15

```
cctggcacca ccaccaatga gtggttggcg gaggtgggcc gcgtcctgtt cccgcctctc      60
cagttaaggc cgctggtgtg agccggggct ctgcgcgagc gagggacgac ggaagggacg     120
ggcaggtgtg ggcgcgggc cacgcagccc gacggcggga gtcgcaggtg ctgggtgcat     180
gggccagtga ggacgcacag agatccctcg ccgcgcggag gaggagcagc gcgggagcca     240
```

```
ggcgctgccc caagaccctg cctgcgtccg agcgagcgga acctcgcgct tcgcccgggg      300
acaatccgaa gtccgcgcta tggaagagga gaaatatttg cctgagctga tggcagagaa      360
agatagcctg gatccatctt ttgtgcatgc gtcgcgcctt ttggcagaag gtaggacttg      420
cc                                                                     422
```

<210> SEQ ID NO 16
<211> LENGTH: 339
<212> TYPE: DNA
<213> ORGANISM: Homo sapiens

<400> SEQUENCE: 16

```
gctaacaaag ctgggttcct gctgggcccc gccctgctcc tcgccccgc gactgggctg        60 ggcgcgctgt ccctagcgc agctatgtcc cgagcgcgcc cccacctgtg cgttaatcta       120
ctgggaatgg gggtggactg cgccttacct ggggcggggt ggggcttaag gagtggtcga      180
gactgaggcg gggtgggagg ttcaggttcc cggggcgcct tccccaaccc gccccgcttt      240
ccccgtccct ccacgcgcac cctgcctgtg gtttccgtgc gccccggcc tgagggctct       300 gggcggcacc ttaacccgga gggcctggag gtctgcacc                             339
```

<210> SEQ ID NO 17
<211> LENGTH: 38
<212> TYPE: DNA
<213> ORGANISM: Artificial Sequence
<220> FEATURE:
<223> OTHER INFORMATION: Artificially synthesized primer sequence
      (SLC13A5_MA_10 forward primer for using MassARRAY assay)

<400> SEQUENCE: 17

```
aggaagagag gaaggatttg aatttggaga tatagtttt                              38
```

<210> SEQ ID NO 18
<211> LENGTH: 56
<212> TYPE: DNA
<213> ORGANISM: Artificial Sequence
<220> FEATURE:
<223> OTHER INFORMATION: Artificially synthesized primer sequence
      (SLC13A5_MA_10 reverse primer for using MassARRAY assay)

<400> SEQUENCE: 18

```
cagtaatacg actcactata gggagaaggc taaaaaaccc aaaaacctac aaaaaa           56
```

<210> SEQ ID NO 19
<211> LENGTH: 32
<212> TYPE: DNA
<213> ORGANISM: Artificial Sequence
<220> FEATURE:
<223> OTHER INFORMATION: Artificially synthesized primer sequence
      (SLC13A5_MA_13 forward primer for using MassARRAY assay)

<400> SEQUENCE: 19

```
aggaagagag ttttttttggg ttttgaaggg tt                                    32
```

<210> SEQ ID NO 20
<211> LENGTH: 57
<212> TYPE: DNA
<213> ORGANISM: Artificial Sequence
<220> FEATURE:
<223> OTHER INFORMATION: Artificially synthesized primer sequence
      (SLC13A5_MA_13 reverse primer for using MassARRAY assay)

<400> SEQUENCE: 20

```
cagtaatacg actcactata gggagaaggc tttatatccc ttcctctcta aaactcc          57
```

<210> SEQ ID NO 21
<211> LENGTH: 32
<212> TYPE: DNA
<213> ORGANISM: Artificial Sequence
<220> FEATURE:
<223> OTHER INFORMATION: Artificially synthesized primer sequence
    (SLC13A5_MA_15 forward primer for using MassARRAY assay)

<400> SEQUENCE: 21
aggaagagag ttttttttgt tttaggggtt gt                                32

<210> SEQ ID NO 22
<211> LENGTH: 55
<212> TYPE: DNA
<213> ORGANISM: Artificial Sequence
<220> FEATURE:
<223> OTHER INFORMATION: Artificially synthesized primer sequence
    (SLC13A5_MA_15 reverse primer for using MassARRAY assay)

<400> SEQUENCE: 22
cagtaatacg actcactata gggagaaggc tccaccaaca taaataaaac tcccc        55

<210> SEQ ID NO 23
<211> LENGTH: 34
<212> TYPE: DNA
<213> ORGANISM: Artificial Sequence
<220> FEATURE:
<223> OTHER INFORMATION: Artificially synthesized primer sequence
    (FAM150A_MA_14 forward primer for using MassARRAY assay)

<400> SEQUENCE: 23
aggaagagag gggaggattt agtagggtaa ttgt                              34

<210> SEQ ID NO 24
<211> LENGTH: 56
<212> TYPE: DNA
<213> ORGANISM: Artificial Sequence
<220> FEATURE:
<223> OTHER INFORMATION: Artificially synthesized primer sequence
    (FAM150A_MA_14 reverse primer for using MassARRAY assay)

<400> SEQUENCE: 24
cagtaatacg actcactata gggagaaggc ttttcaccta aaaaaacact aaaacc       56

<210> SEQ ID NO 25
<211> LENGTH: 36
<212> TYPE: DNA
<213> ORGANISM: Artificial Sequence
<220> FEATURE:
<223> OTHER INFORMATION: Artificially synthesized primer sequence
    (GRM6_MA_8 forward primer for using MassARRAY assay)

<400> SEQUENCE: 25
aggaagagag ggtttaggat aagtttgtga tagatg                            36

<210> SEQ ID NO 26
<211> LENGTH: 56
<212> TYPE: DNA
<213> ORGANISM: Artificial Sequence
<220> FEATURE:
<223> OTHER INFORMATION: Artificially synthesized primer sequence
    (GRM6_MA_8 reverse primer for using MassARRAY assay)

<400> SEQUENCE: 26
cagtaatacg actcactata gggagaaggc taaaacaaaa aaacaaaccc aaaaat       56

<210> SEQ ID NO 27
<211> LENGTH: 33
<212> TYPE: DNA
<213> ORGANISM: Artificial Sequence
<220> FEATURE:
<223> OTHER INFORMATION: Artificially synthesized primer sequence
      (ZFP42_MA_2 forward primer for using MassARRAY assay)

<400> SEQUENCE: 27
aggaagagag gagttgatgg gtggttgtag ttt                            33

<210> SEQ ID NO 28
<211> LENGTH: 60
<212> TYPE: DNA
<213> ORGANISM: Artificial Sequence
<220> FEATURE:
<223> OTHER INFORMATION: Artificially synthesized primer sequence
      (ZFP42_MA_2 reverse primer for using MassARRAY assay)

<400> SEQUENCE: 28
cagtaatacg actcactata gggagaaggc tcccatttaa aaaaaattcc ataaaacaaa    60

<210> SEQ ID NO 29
<211> LENGTH: 40
<212> TYPE: DNA
<213> ORGANISM: Artificial Sequence
<220> FEATURE:
<223> OTHER INFORMATION: Artificially synthesized primer sequence
      (ZNF154_MA_5 forward primer for using MassARRAY assay)

<400> SEQUENCE: 29
aggaagagag ggtgaatata ttttagagaa gttaaaatgg                     40

<210> SEQ ID NO 30
<211> LENGTH: 56
<212> TYPE: DNA
<213> ORGANISM: Artificial Sequence
<220> FEATURE:
<223> OTHER INFORMATION: Artificially synthesized primer sequence
      (ZNF154_MA_5 reverse primer for using MassARRAY assay)

<400> SEQUENCE: 30
cagtaatacg actcactata gggagaaggc ttccctccac taccctaaaa cttaaa        56

<210> SEQ ID NO 31
<211> LENGTH: 35
<212> TYPE: DNA
<213> ORGANISM: Artificial Sequence
<220> FEATURE:
<223> OTHER INFORMATION: Artificially synthesized primer sequence
      (RIMS4_MA_9 forward primer for using MassARRAY assay)

<400> SEQUENCE: 31
aggaagagag ggagttttag tttatgaggg aagga                          35

<210> SEQ ID NO 32
<211> LENGTH: 54
<212> TYPE: DNA
<213> ORGANISM: Artificial Sequence
<220> FEATURE:
<223> OTHER INFORMATION: Artificially synthesized primer sequence
      (RIMS4_MA_9 reverse primer for using MassARRAY assay)

<400> SEQUENCE: 32
cagtaatacg actcactata gggagaaggc taaaccccaa aatctccaaa atac          54

<210> SEQ ID NO 33
<211> LENGTH: 37
<212> TYPE: DNA
<213> ORGANISM: Artificial Sequence
<220> FEATURE:
<223> OTHER INFORMATION: Artificially synthesized primer sequence
      (TRH_MA_8 forward primer for using MassARRAY assay)

<400> SEQUENCE: 33
aggaagagag aatagatttt tagaggtggt gtagaaa                                37

<210> SEQ ID NO 34
<211> LENGTH: 55
<212> TYPE: DNA
<213> ORGANISM: Artificial Sequence
<220> FEATURE:
<223> OTHER INFORMATION: Artificially synthesized primer sequence
      (TRH_MA_8 reverse primer for using MassARRAY assay)

<400> SEQUENCE: 34
cagtaatacg actcactata gggagaaggc taaaaaactc cctttccaat actcc           55

<210> SEQ ID NO 35
<211> LENGTH: 37
<212> TYPE: DNA
<213> ORGANISM: Artificial Sequence
<220> FEATURE:
<223> OTHER INFORMATION: Artificially synthesized primer sequence
      (ZNF540_MA_17 forward primer for using MassARRAY assay)

<400> SEQUENCE: 35
aggaagagag gggtagggta gaattaggtt aaagaaa                                37

<210> SEQ ID NO 36
<211> LENGTH: 56
<212> TYPE: DNA
<213> ORGANISM: Artificial Sequence
<220> FEATURE:
<223> OTHER INFORMATION: Artificially synthesized primer sequence
      (ZNF540_MA_17 reverse primer for using MassARRAY assay)

<400> SEQUENCE: 36
cagtaatacg actcactata gggagaaggc tactaaaatc aataacccccc aaaaaa         56

<210> SEQ ID NO 37
<211> LENGTH: 35
<212> TYPE: DNA
<213> ORGANISM: Artificial Sequence
<220> FEATURE:
<223> OTHER INFORMATION: Artificially synthesized primer sequence
      (PCDHAC1_MA_5 forward primer for using MassARRAY assay)

<400> SEQUENCE: 37
aggaagagag tggtagtttt tgggatataa gaggg                                  35

<210> SEQ ID NO 38
<211> LENGTH: 56
<212> TYPE: DNA
<213> ORGANISM: Artificial Sequence
<220> FEATURE:
<223> OTHER INFORMATION: Artificially synthesized primer sequence
      (PCDHAC1_MA_5 reverse primer for using MassARRAY assay)

<400> SEQUENCE: 38
cagtaatacg actcactata gggagaaggc taaactaccc aaatcttaac ctccac          56

<210> SEQ ID NO 39

```
<211> LENGTH: 37
<212> TYPE: DNA
<213> ORGANISM: Artificial Sequence
<220> FEATURE:
<223> OTHER INFORMATION: Artificially synthesized primer sequence
      (PRAC_MA_2 forward primer for using MassARRAY assay)

<400> SEQUENCE: 39
aggaagagag ggtgaaagtt tgttgtttat tttttt                              37

<210> SEQ ID NO 40
<211> LENGTH: 56
<212> TYPE: DNA
<213> ORGANISM: Artificial Sequence
<220> FEATURE:
<223> OTHER INFORMATION: Artificially synthesized primer sequence
      (PRAC_MA_2 reverse primer for using MassARRAY assay)

<400> SEQUENCE: 40
cagtaatacg actcactata gggagaaggc tcaaactaaa ttctaatccc caccctt       56

<210> SEQ ID NO 41
<211> LENGTH: 35
<212> TYPE: DNA
<213> ORGANISM: Artificial Sequence
<220> FEATURE:
<223> OTHER INFORMATION: Artificially synthesized primer sequence
      (ZNF671_MA_8 forward primer for using MassARRAY assay)

<400> SEQUENCE: 41
aggaagagag tgggatatag gggttgtagg tattt                               35

<210> SEQ ID NO 42
<211> LENGTH: 56
<212> TYPE: DNA
<213> ORGANISM: Artificial Sequence
<220> FEATURE:
<223> OTHER INFORMATION: Artificially synthesized primer sequence
      (ZNF671_MA_8 reverse primer for using MassARRAY assay)

<400> SEQUENCE: 42
cagtaatacg actcactata gggagaaggc tataaaaacc acactctacc cacaaa        56

<210> SEQ ID NO 43
<211> LENGTH: 35
<212> TYPE: DNA
<213> ORGANISM: Artificial Sequence
<220> FEATURE:
<223> OTHER INFORMATION: Artificially synthesized primer sequence
      (WNT3A_MA_9 forward primer for using MassARRAY assay)

<400> SEQUENCE: 43
aggaagagag gtttatttgg taatgagggg ttgtt                               35

<210> SEQ ID NO 44
<211> LENGTH: 56
<212> TYPE: DNA
<213> ORGANISM: Artificial Sequence
<220> FEATURE:
<223> OTHER INFORMATION: Artificially synthesized primer sequence
      (WNT3A_MA_9 reverse primer for using MassARRAY assay)

<400> SEQUENCE: 44
cagtaatacg actcactata gggagaaggc tttcctcaat cttaaacatc tcaaaa        56

<210> SEQ ID NO 45
<211> LENGTH: 38
```

```
<212> TYPE: DNA
<213> ORGANISM: Artificial Sequence
<220> FEATURE:
<223> OTHER INFORMATION: Artificially synthesized primer sequence
      (KHDRBS2_MA_19(rev) forward primer for using MassARRAY assay)

<400> SEQUENCE: 45
aggaagagag tttggtatta ttattaatga gtggttgg                              38

<210> SEQ ID NO 46
<211> LENGTH: 57
<212> TYPE: DNA
<213> ORGANISM: Artificial Sequence
<220> FEATURE:
<223> OTHER INFORMATION: Artificially synthesized primer sequence
      (KHDRBS2_MA_19(rev) reverse primer for using MassARRAY assay)

<400> SEQUENCE: 46
cagtaatacg actcactata gggagaaggc taacaaatcc taccttctac caaaaaa        57

<210> SEQ ID NO 47
<211> LENGTH: 35
<212> TYPE: DNA
<213> ORGANISM: Artificial Sequence
<220> FEATURE:
<223> OTHER INFORMATION: Artificially synthesized primer sequence
      (ASCL2_MA_8 forward primer for using MassARRAY assay)

<400> SEQUENCE: 47
aggaagagag gttaataaag ttgggttttt gttgg                                 35

<210> SEQ ID NO 48
<211> LENGTH: 53
<212> TYPE: DNA
<213> ORGANISM: Artificial Sequence
<220> FEATURE:
<223> OTHER INFORMATION: Artificially synthesized primer sequence
      (ASCL2_MA_8 reverse primer for using MassARRAY assay)

<400> SEQUENCE: 48
cagtaatacg actcactata gggagaaggc taatacaaac ctccaaaccc tcc             53

<210> SEQ ID NO 49
<211> LENGTH: 384
<212> TYPE: DNA
<213> ORGANISM: Homo sapiens

<400> SEQUENCE: 49
gggaggaccc agtagggtaa ctgctgtgtt gccctggtgg ttctccctgg gctctgtctc       60
ctgctgcctc caccccctga gccttggggt ctgtcatggc ttcccctggc tggtggggtc      120
agtagaacct gtggtgccta ggtctggatg gaaaaaagca gggctggggt gtggcctgga     180
tgagtggaga tctctgtgcc ttgggctcaa aggtgtgggg tgtgctctgc tgctgagccc     240
ctgcttgctc aggaacactg gccatgctgt catgccagct gccccctgcc caggtctgga     300
ggcctgacct gctctcctag gtgcagcact gtgttctctt ctgtgtgggg gagtggtggg     360
tggaagaggt ctggggctgg gcac                                            384

<210> SEQ ID NO 50
<211> LENGTH: 384
<212> TYPE: DNA
<213> ORGANISM: Homo sapiens

<400> SEQUENCE: 50
```

```
gggaggaccc agtagggtaa ctgccgcgtc gccccggcgg ttctccctgg gctctgtctc    60
ccgccgcctc cacccccga gcctcggggt ccgtcacggc ttcccctggc tggcggggtc   120
agtagaaccc gcggcgccta ggtccggacg gaaaaaagca gggccggggt gcggcctgga   180
tgagcggaga tctccgcgcc ttgggctcaa aggtgcgggg tgcgctctgc tgccgagccc   240
ctgctcgctc aggaacactg gccacgccgt cacgccagcc gcccctgccc caggtctgga   300
ggcccgacct gctctcctag gcgcagcacc gcgttctctt ccgcgtgggg gagcggcggg   360
cggaagaggt ctggggctgg gcac                                         384

<210> SEQ ID NO 51
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 51
gggaggattt agtagggtaa ttgt                                          24

<210> SEQ ID NO 52
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 52
atacccaacc ccaaacctct tc                                            22
```